US009970944B2

(12) United States Patent
Schmitz et al.

(10) Patent No.: US 9,970,944 B2
(45) Date of Patent: May 15, 2018

(54) METHODS OF MODULATING CYTOKINE ACTIVITY; RELATED REAGENTS

(71) Applicant: Merck Sharp & Dohme Corp., Rahway, NJ (US)

(72) Inventors: Jochen Schmitz, San Francisco, CA (US); Martin Oft, Palo Alto, CA (US); Robert A. Kastelein, Portola Valley, CA (US); J. Fernando Bazan, Menlo Park, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 579 days.

(21) Appl. No.: 14/171,629

(22) Filed: Feb. 3, 2014

(65) Prior Publication Data

US 2014/0140954 A1 May 22, 2014

Related U.S. Application Data

(63) Continuation of application No. 12/239,689, filed on Sep. 26, 2008, now abandoned, which is a continuation of application No. 11/682,224, filed on Mar. 5, 2007, now abandoned, which is a (Continued)

(51) Int. Cl.

| | |
|---|---|
| ***A61K 38/00*** | (2006.01) |
| ***C07K 14/00*** | (2006.01) |
| ***G01N 33/68*** | (2006.01) |
| ***C07K 16/24*** | (2006.01) |
| ***C07K 16/28*** | (2006.01) |

(Continued)

(52) U.S. Cl.

CPC ......... *G01N 33/6869* (2013.01); *A61K 38/20* (2013.01); *C07K 16/244* (2013.01); *C07K 16/2866* (2013.01); *A61K 38/00* (2013.01); *A61K 2039/505* (2013.01); *C07K 2317/76* (2013.01)

(58) Field of Classification Search

CPC .. G01N 33/6869; A61K 38/20; C07K 16/244; C07K 16/2866

See application file for complete search history.

(56) References Cited

U.S. PATENT DOCUMENTS

| | | | |
|---|---|---|---|
| 5,116,964 | A | 5/1992 | Capon et al. |
| 5,576,191 | A | 11/1996 | Gayle et al. |
| 6,323,334 | B1 | 11/2001 | Kingsbury et al. |

(Continued)

FOREIGN PATENT DOCUMENTS

| | | | |
|---|---|---|---|
| EP | 1 110 969 | A1 | 6/2001 |
| WO | WO 91/08298 | A2 | 6/1991 |

(Continued)

OTHER PUBLICATIONS

Johnson et al., (Am J Resp Crit Care Med Feb. 1, 2004, 169(4):378-385—Epub Nov. 3, 2003).*

(Continued)

*Primary Examiner* — Cherie M Stanfield

(74) *Attorney, Agent, or Firm* — Gloria M. Fuentes; Li Su

(57) ABSTRACT

Provided are methods of modulating cytokine activity, e.g., for the purpose of treating immune and inflammatory disorders, including tumors and cancer. Also provided are methods of administering agonists or antagonists of IL-33 and IL-33 receptor.

8 Claims, 3 Drawing Sheets disease score

Isotype
anti-IL-33

CIA disease score days

Related U.S. Application Data continuation of application No. 11/059,117, filed on Feb. 15, 2005, now abandoned.

(60) Provisional application No. 60/545,730, filed on Feb. 17, 2004.

(51) Int. Cl.
*A61K 38/20* (2006.01)
*A61K 39/00* (2006.01)

(56) References Cited

U.S. PATENT DOCUMENTS

| | | |
|---|---|---|
| 8,187,596 B1 | 5/2012 | Chackerian et al. |
| 2004/0009481 A1 | 1/2004 | Schlegel et al. |

FOREIGN PATENT DOCUMENTS

| | | | |
|---|---|---|---|
| WO | WO 92/10210 | 6/1992 | |
| WO | WO 95/01997 A1 | 1/1995 | |
| WO | WO 99/32626 | 7/1999 | |
| WO | WO 99/34217 A | 7/1999 | |
| WO | WO 01/46697 | 6/2001 | |
| WO | WO 02/16436 | 2/2002 | |
| WO | WO 02/46475 A2 | 6/2002 | |
| WO | WO 2003/016475 A2 | 2/2003 | |
| WO | WO 2004/056868 A2 | 7/2004 | |
| WO | WO 2004056868 A2 * | 7/2004 | ............. C07K 14/47 |
| WO | WO 05/067667 | 7/2005 | |
| WO | WO 2008/144610 | 5/2008 | |

OTHER PUBLICATIONS

Information Hyperlinked Over Protieins. IL-33/NF-HEV. (www.ihop-netorg/UniPub/iHOP/gismo/104813.html?ORGANISM_ID=1) last accessed Jun. 27, 2017.*

NCBI Gene—IL-33/NF-HE. Gene ID 90865 (www.ncbi.nlm.nih.gov/entrez/query.fcgi?db=Gene&term=90865). Last accessed Jun. 27, 2017.*

Apte and Voronov (2002) *Sem. Cancer Biol.* 12:277-290 "Interleukin-1—a major pleiotropic cytokine in tumor-host interactions".

Attur, et al. (2000) *J. Biol. Chem.* 51:40307-40315 "Reversal of autocrine and paracrine effects of Interleukin 1 (IL-1) in human arthritis by type II decoy receptor".

Baekkevold, et al. & Onda, et al., GenBank Accession No. NM_033439, May 14, 2005 Definition: *Homo sapiens* chromosome 9 open reading frame 26 (NF-HEV) (C9orf26), mRNA.

Chackerian, ET. (2007) *J. Immunology* 179:2551-2555 "IL-1 receptor accessory protein and ST2 comprise the IL-33 receptor complex".

Choy and Panayi (2001) *New Engl. J. Med.* 344:907-916 "Cytokine pathways and joint inflammation in rheumatoid arthritis".

Chung (2001) *Eur. Resp. J. Suppl.* 34: 50s-59s "Cytokines in chronic obstructive pulmonary disease".

Clark et al. & Thomassen et al., GenBank Accession No. NM_021805, Apr. 22, 2005 Definition: *Homo sapiens* single Ig IL-1R-related molecule (SIGIRR), mRNA.

Clark et al. & Thomassen et al., GenBank Accession No. NP_068577, Apr. 22, 2005 Definition: single Ig IL-1R-related molecule [*Homo sapiens*].

Clark, et al. (2003) *Genome Res.* 13:2265-2270 "The secreted protein discovery initiative (SPDI), a large-scale effort to identify novel human secreted and transmembrane proteins: a bioinformatics assessment".

Coyle, et al. (1999) *J. Exp. Med.* 190:895-902 "Crucial role of the interleukin 1 receptor family member T1/ST2 in T helper cell type 2-mediated lung mucosal immune responses".

Debets, et al. (1997) *J. Immunol.* 158:2955-2963 "The IL-1 system in psoriatic skin: IL-1 antagonist sphere of influence in lesional psoriatic epidermis".

Debets, et al. (2001) *J. Immunol.* 167:1440-1446 "Two novel IL-1 family members, IL-1δ and IL-1, function as an antagonist and agonist of NF-κb activation through the orphan IL-1ε receptor-related protein 2".

Dinarello (2000) *Chest* 118:503-508 "Proinflammatory Cytokines".

Dinarello, et al. (1998) *J. Leuko. Biol.* 63:658-664 "Overview of interleukin-18: more than an interferon-γ inducing factor".

Feldmann and Maini (2001) *Annu. Rev. Immunol.* 19:163-196 "Anti-TNFα therapy of rheumatoid arthritis: what have we learned?".

Freeman and Buchman (2001) *Expert Opin. Biol. Ther.* 1:301-308 "Interleukin-1 receptor antagonist as therapy for inflammatory disorders".

Garcia-Sastre (2001) *Virology* 279:375-384 "Inhibition of interferon-mediated antiviral responses by influenza A viruses and other negative-strand RNA viruses".

Garlanda et al., GenBank Accession No. NM_023059, Apr. 15, 2005 Definition: Mus musculus expressed sequence AI256711 (AI256711) mRNA.

Garlanda et al., GenBank Accession No. NP_075546, Apr. 15, 2005 Definition: single Ig IL-1 receptor related protein [Mus musculus].

Garlanda, et al. (2004) *Proc. Natl. Acad. Sci.* 101:3522-3526 "Intestinal inflammation in mice deficient in Tir8, an inhibitory member of the IL-1 receptor family".

Hoshino, et al. (1999) *J. Exp. Med.* 190:1541-1547 "The absence of interleukin 1 receptor-related T1/ST2 does not affect T helper cell type 2 development and its effector function".

Irikura, et al. (2002) *New EngL J. Med.* 169:393-398 "The epistatic interrelationships of IL-1, IL-1 receptor antagonist, and the type I IL-1 receptor".

Janeway, el al. (2001) *Immunobiology*, Fifth Edition, Chapter 12, pp. 471-500.

Johnson, et at. (2004) *Am. J. Respir. Crit. Care Med.* 169:378-385 "Continuous exposure to house dust mite elicits chronic airway inflammation and structural remodeling".

Katze, etal. (2002) *Nat. Rev. Immunol.* 2:675-687 "Viruses and interferon: a fight for supremacy".

Kaufmann, et al. (2001) *Immunobiol.* 204:603-613 "Defense against influenza A virus infection: essential role of the chemokine system".

Kim, et al. (2002) *J. Biol. Chem.* 277:10998-11003 "Identification of amino acid residues critical for biological activity in human interleukin-18".

Koudssi, et al. (1998) *J. Biol. Chem.* 273: 25796-25803 "Cardiac fibroblasts arrest at the $G_1$/S restriction point in response to interleukin (IL)-1β".

Krause, et al. (2002) *J. Immunol.* 169:6610-6616 "Rheumatoid arthritis synoviocyte survival is depencent on Stat3".

Kropf, et al. (2002) *Eur. J. Immunol.* 32:2450-2459 "Organ-specific distribution of CD4+ T1/ST2+ Th2 cells in Leishmania major infection".

Kropf, et al. (2002) *Infect. Immunity* 70:5512-5520 "Identification of two distinct subpopulations of Leishmania major-specific T helper 2 cells".

Kropf, et al. (2003) *Infect. Immunity* 71:1961-1971 "Signaling through the T1/ST2 molecule is not necessary for Th2 differentiation but is important for the regulation of type 1 responses in nonhealing Leishmania major infection".

Lacey, et al. (2003) *Arthritis Rheum.* 48: 103-109 "Control of fibroblast-like synoviocyte proliferation by macrophage migration inhibitory factor".

Lecart, et al. (2002) *Eur. J. Immunol.* 32:2979-2987 "Activated, but not resting human Th2 cells, in contrast to Th1 and T regulatory cells, produce soluble ST2 and express low levels of ST2L at the cell surface".

Lohning, et al. (1998) *Proc. Natl. Acad. Sci.* USA 95:6930-6935 "T1/ST2 is preferentially expressed on murine Th2 cells, independent of interleukin 4, interleukin 5, and interleukin 10, and important for Th2 effector function".

(56) References Cited

OTHER PUBLICATIONS

Lohning, et al. (1999) *J. Immunol.* 162:3882-3889 "T1/ST2 expression is enhanced on CD4+ T cells from schistosome egg-induced granulomas: analysis of Th cell cytokine coexpression ex vivo".
McMahon, et al. (1997) *J. Biol. Chem.* 272:28202-28205 "Intracellular precursor interleukin (IL)-1α, but not mature IL-1α, is able to regulate human endothelial cell migration in vitro".
Mitcham, et al. (1996) *J. Biol. Chem.* 271:5777-5783 "T1/ST2 signaling establishes it as a member of an expanding interleukin-1 receptor family".
Murai, et al. (2001) *J. Biol. Chem.* 276:6797-6806 "Altered regulation of cell cycle machinery involved in interleukin-1-induced $G_1$ and $G_2$ phase growth arrest of A37552 human melanoma cells".
Nesbit, et al. (1999) *Oncogene* 18:6469-6476 "Basic fibroblast growth factor induces a transformed phenotype in normal human melanocytes".
Niki, et al. (2001) *J. Clin. Invest.* 107:1127-1135 "Macrophage- and neutrophils-dominant arthritis in human IL-1α transgenic mice".
Osawa, et al. (2000) *J. Biochem. 127:883-893 "IL-1 induces expression of* $p21^{WAF1}$ independently of p53 in high-passage human embryonic fibroblasts WI38".
Saijo, et al. (2002) *J. Immunol.* 169: 469-475 "Proinflammatory cytokine IL-1β promotes tumor growth of lewis lung carcinoma by induction of angiogenic factors: in vivo analysis of tumor-stromal interaction".
Schmitz, et al. (2005) *Immunity* 23:479-490 "IL-33, an Interleukin-1-like Cytokine that Signals via the IL-1 Receptor-Related Protein ST2 and Induces T Helper Type 2-Associated Cytokines".
Suarez and Schultz-Cheery (2000) *Dev. Comp. Immunol.* 24:269-283 "Immunology of avian influenza virus: a review".
Senn, et al. (2000) *Eur. J. Immunol.* 30:1929-1938 "T1-defident and T1-Fc-transgenic mice develop a normal protective Th2-type immune response following infection with Nippostrongylus brasiliensis".
Sweet, et al. (2001) *J. Immunol.* 166:6633-6639 "A novel pathway regulating lipopolysaccharide-induced shock by ST2/T1 via inhibition of toll-like receptor 4 expression".
Swirski, et al. (2002) *J. Immunol.* 169:3499-3506 "Chronic exposure to innocuous antigen in sensitized mice leads to suppressed airway eosinophilia that is reversed by granulocyte macrophage colony-stimulating factor".
Thomassen et al. (1999) *Cytokine* 11:389-399 "Identification and characterization of SIGIRR, a molecule representing a novel subtype of the IL-1R superfamily".
Townsend, et al. (2000) *J. Exp. Med.* 191:1069-1075 "T1/ST2-deficient mice demonstrate the importance of T1/ST2 in developing primary T helper cell type 2 responses".
Tripp (2003) *Curr. Pharm. Des.* 9:51-59 "Role of cytokines in the development and maintenance of memory T cells during respiratory viral infection".
Van Reeth (2000) *Vet. Microbiol.* 74:109-116 "Cytokines in the pathogenesis of influenza".
Van Reeth and Nauwynck (2000) *Vet. Res.* 31:187-213 "Proinflammatory cytokines and viral respiratory disease in pigs".
Walzl, et al. (2001) *J. Exp. Med.* 193:785-792 "Inhibition of T1/ST2 during respiratory syncytial virus infection prevents T helper cell type 2 (Th2)—but not Th1-driven immunopathology".
Williams, et al. (2000) *J. Immunol.* 165: 7240-7245 "Evaluation of TNF-α and IL-1 blockade in collagen-induced arthritis and comparison with combined anti-TNF-α/anti-CD4 therapy".
Wong, et al. (1997) *Proc. Natl. Acad. Sci. USA* 94:227-232 "Interleukin (IL) 1β, IL-1 receptor antagonist, IL-10, and IL-13 gene expression in the central nervous system and anterior pituitary during systemic inflammation: pathophysiological implications".
Woolley (2003) *New Engl. J. Med.* 348:1709-1711 "The mast cell in inflammatory arthritis".
Xu, et al. (1998) *J. Exp. Med.* 187:787-794 "Selective expression of a stable cell surface molecule on Type 2 but not Type 1 helper T cells".
Yoshida, et al. (2002) *Brit. J. Cancer* 86:1396-1400 "Interleukin-6, tumour necrosis factor α and interleukin-1β in patients with renal cell carcinoma".
You, et al. (2001) *J. Exp. Med.* 193:101-109 "Modulation of the nuclear factor κB pathway by Shp-2 tyrosine phosphatase in mediating the induction of Interleukin (IL)-6 by IL-1 or tumor necrosis factor".
Zeisler, et al. (1998) *Eur. J. Cancer* 34:931-933 "Serum interleukin 1 in ovarian cancer patients".
Zeki, et al. (1999) *J. Endocrinol.* 160:67-73 "Interleukin-1α regulates $G_1$, cell cycle progression and arrest in thyroid carcinoma cell lines NIM1 and NPA".
Cayrol and Girard (2009) *Proc Natl Acad Sci U S A*, 106(22):9021-6. Epub May 13, 2009. "The IL-1-like cytokine IL-33 is inactivated after maturation by caspase-1".
Baekkevold, et al. (2003) *American J. of Pathology* 163(1):69-79, "Molecular characterization of NF-HEV, a nuclear factor preferentially expressed in human high endothelial venules".
Communication from the Examining Division pursuant to Art. 94(3) EPC dated Jul. 7, 2009.
D'Arienzo et al., "Allergy and Mucosal Eosinophil Infiltrate in Ulcerative Colitis" SC and J Gastroenterol, vol. 35, 2000.
Devos et al. "Interleukin-5 and its receptor: a drug target for eosinophilia associated with chronic allergic disease" J Leukoc Biol 57:813 (1995).
Kumar et al., "Expression of ST2, an Interleukin-1 Receptor Homologue, Is Induced by Proinflammatory Stimuli" Biochemical and Biophysical Communications, vol. 235, No. 976810, 1997.
Kumar et al., "ST2IT1 Protein Functionally Binds to Two Secreted Proteins from Balb/c 3T3 and Human Umbilical Vein Endothelial Cells but Does Not Bind Interleukin 1*" The Journal of Biological Chemistry, vol. 270, No. 46, 1995.
Masuda et al., "Molecular profile of synovial fibroblasts in rheumatoid arthritis depends on the stage of proliferation" Arthritis Research, vol. 4, 2002.
Miller "Role of IL-33 in inflammation and disease" J. Inflammation 8:22 (2011).
Onda et al.: "Identification of genes differentially expressed in canine vasospastic cerebral arteries after subarachnoid hemorrhage", Journal of Cerebral Blood and Flow Metabolism, vol. 19, pp. 1279-1288, Lippincott Williams & Wilkins, Inc., Phil., USA (May 12, 1999).
O'Neill, "SIGIRR puis the breaks on Toll-/ike receptors" Nature Immunology, vol. 4, No. 9, Sep. 9, 2003.
Opalinska and Gewirtz, "Nucleic-acid therapeutics: Jul. 2002 basic principles and recent applications", Nature Reviews: Drug Discovery, vol. 1, pp. 503-514, Nature Publishing Group.
Oshikawa et al., "Elevated Soluble ST2 Protein Levels in Sera of Patients with Asthma with an Acute Exacerbation" American Journal of Respiratory and Critical care Medicine, vol. 164, 2001.
Oshikawa et al., "Expression and function of the ST2 gene in a murine model of allergic airway inflammation" Blackwell Science Ltd, vol. 32, 2002.
Scaffidi et al. "Release of chromatin protein HMGB1 by necrotic cells triggers inflammation" Nature 418:191-195 (2002).
Sims, "IL-1 and IL-18 receptors, and their extended family" Elsevier SCiences Ltd, *Current Opinion in Immunology* 14:117-122 (2002).
Southern Biotech Catalogue, "Human Interteukin-33 (IL-33) Recombinant Protein" Southern Biotech Catalogue, 2009.
UniProt, "095760 (IL33_HUMAN)", Host: www.uniprot.org, Sep. 21, 2011
UniProt, "UniProtKB Entry 095760—History", Host: www.uniprot.org, Oct. 14, 2011.
Van Zate and Rosen, "Sulphated endothelial ligands for L-selectin in lymphocyte homing and inflammation", Biochemical Society, (2003) vol. 31, part 2, pp. 313-317.
Information Hyperlinked Over Proteins (IHOP)—IL-33—www.ihop-net.org/UniPub/IHOP/gismo/104813:html?ORGANISM_ID=1 Last accessed Jan. 4, 2010.
Oct. 4, 2016—Reply to Appeal in Opposition to EP1725261.
May 13, 2016—Statement of Grounds of Appeal of Regeneron Pharmaceuticals, Inc. in Opposition to EP1725261.

(56) References Cited

OTHER PUBLICATIONS

May 13, 2016—Statement of Grounds of Appeal of Takeda California, Inc. in Opposition to EP1725261.
May 5, 2016—Statement of Grounds of Appeal of Sanofi in Opposition to EP1725261.
Jan. 5, 2016—Decision of the Opposition Division and instruction in EP Opposition to EP1725261.
Jan. 5, 2016—Grounds for the Decision (Annex)—Opposition in EP Opposition to EP1725261.
Jan. 5, 2016—Scanned Annex to a Communication—Opposition Procedure in EP Opposition to EP 1725261.
Jan. 7, 2015—Annex to Communication—Opposition in EP Opposition to EP1725261.
Sep. 12, 2014—Letter Regarding the Opposition Procedure of Opponent in EP Opposition to EP 1725261.
Sep. 12, 2014—Letter Regarding the Opposition Procedure of Opponent IV in EP Opposition to EP 1725261.
Sep. 12, 2014—Letter Regarding the Opposition Procedure of Opponent V in EP Opposition to EP 1725261.
Sep. 12, 2014—Letter Regarding the Opposition Procedure of Opponent II in EP Opposition to EP 1725261.
Aug. 26, 2016—Non-Patent Literature Cited During the Opposition Procedure in EP Opposition to EP 1725261.
Sonnhammer et al., Pfam: A Comprehensive Database of Protein Domain Families Based on Seed Alignment, Proteins, 28:405-420 (1997)—Aug. 14, 2014—Non-Patent Literature Cited During the Opposition Procedure in EP Opposition to EP 1725261.
Karplus, et al., Hidden Markov Models for Detecting Remote Protein Homologies, Bioinformatics, vol. 14, No. 10, pp. 846-856 (1998)—Aug. 14, 2014—Non-Patent Literature Cited During the Opposition Procedure in EP Opposition to EP 1725261.
Park et al., Intermediate Sequences Increase the Detection of Homology Between Sequences, J. Mol. Biol. 273:349-34 (1997)—Aug. 14, 2014—Non-Patent Literature Cited During the Opposition Procedure in EP Opposition to EP 1725261.
Apr. 22, 2014—Annex to the Communication—Opposition in EP Opposition to EP 1725261.
Oct. 16, 2013—Citation in Opposition Procedure in EP Opposition to EP 1725261.
Jul. 2, 2012—Citation in Opposition to Procedure in EP Opposition to EP 1725261.
Jul. 2, 2012—Reply of the Patent Proprietor to the Notice(s) of Opposition in EP Opposition to EP 1725261.
Oct. 26, 2011—Citation in Opposition Procedure in EP Opposition to EP 1725261.
Oct. 26, 2011—Filing of a New Opposition in EP Opposition to EP 1725261.
Oct. 26, 2011—Letter Regarding the Opposition Procedure (no time limit) in EP Opposition to EP1725261.
Oct. 24, 2011—Filing of a New Opposition in EP Opposition to EP 1725261.
Sonnhammer et al., Ffam: A Comprehensive Database of Protein Domain Families Based on Seed Alignments, Proteins vol. 28, (1997), pp. 405-420.
Karplus et al., Hidden Markov Models for detecting remote protein homologies, vol. 14, No. 10, (1998), pp. 846-856.
Park et al., Intermediate Sequences Increase the Detection of Homology Between Sequences, Journal of Molecular Biology, vol. 273, (1997), pp. 349-354.
Palmeri et al., Differential gene expression profile of human tonsil high endothelial cells: implications for lymphocyte trafficking, Journal of Leukocyte Biology, vol. 71 (2004), pp. 910-927.
Dunn et al., Annotating genes with potential roles in the immune system: six new members of the IL-1 family, Trends in Immunology, vol. 22, No. 10, (2001, pp. 533-536.
Maier et al., Endogenous Interleukin 1 Alpha Must Be Transported to the Nucleus to Exert Its Activity in Human Endothelial Cells, vol. 14, No. 3, (1994), pp. 1845-1851.
Zhang et al., Nuclear Translocation of the N-terminal Prodomain of Interleukin-16*, Journal of Biological Chemistry, vol. 276, No. 2, (2001), pp. 1299-1303.
Final Rejection, dated Oct. 1, 2013.
Advisory Action (PTOL-303), dated Sep. 13, 2010.
Final Rejection, dated Jul. 2, 2010.
Non-Final Rejection, dated Jan. 11, 2010.
Non-Final Rejection, dated Mar. 28, 2008.
Final Rejection. dated Oct. 4, 2006.
Non-Final Rejection, dated Jan. 24, 2006.
Opposition Against European Pat. No. 1725261—Appeal No. T041916-3.3.04—Submission, Sep. 6, 2017—12 pages.
Declaration of Dr. Jean-Phiippe Girard—8 pages.
Jean-Philippe Girard and Timothy A. Springer, High endothelial venules (HEVs): specialized endothelium for lymphocyte migration, Immunology, vol. 16, No. 9, 1995, 449-457.
A. Ager, Trafficking, BSI Parallel Session Organized and edited by E. Bell (School of Biological Sciences, University of Manchester). 660th Meeting, Joint Congress with British Society for Immunology, held at Harrogate, Dec. 10-13, 1996—421-428.
James F. Sinclair and Alison D. O'Brien, Cell Surface-localized Nucleolin Is a Eukaryotic Receptor for the Adhesin lntimin-y of Enterohemorrhagic *Escherichia coli* O157:H7, The Journal of Biological Chemistry, vol. 277, No. 4, Jan. 25, 2002, 2876-2885.
Said, et al., The Anti-HIV Cytokine Midkine Binds the Cell Surface-expressed Nucleolin as a Low Affinity Receptor, The Journal of Biological Chemistry, vol. 277, No. 40., Oct. 4, 2002, 37492-37502.
Christian et al., Nucleolin expressed at the cell surface is a marker of endothelial cells in angiogenic blood vessels, The Journal of Cell Biology, vol. 163, No. 4, 2003, 871-878.
Chapter 8, Article IV, of Ph.D. thesis of Dr. Espen Baekkevold, publically available on Mar. 2, 2002—25 pages.
Alarcon-Segovia D. et al. (1978) Nature 271, 67-69—3 pages.
Ruiz-Arguelles A. et al. (2003) Current Pharmaceutical Designs, 9(23), 1881-1887.
Sun K.-H et al., (2001) Rheumatology 40, 750-756.

* cited by examiner

SEQUENCE LISTING

```
<160> NUMBER OF SEQ ID NOS: 12

<210> SEQ ID NO 1
<211> LENGTH: 813
<212> TYPE: DNA
<213> ORGANISM: Homo sapiens

<400> SEQUENCE: 1

atgaagccta aaatgaagta ttcaaccaac aaaatttcca cagcaaagtg gaagaacaca      60

gcaagcaaag ccttgtgttt caagctggga aaatcccaac agaaggccaa agaagtttgc     120

cccatgtact ttatgaagct ccgctctggc cttatgataa aaaaggaggc ctgttacttt     180

aggagagaaa ccaccaaaag gccttcactg aaaacaggta gaaagcacaa aagacatctg     240

gtactcgctg cctgtcaaca gcagtctact gtggagtgct ttgcctttgg tatatcaggg     300
```

```
gtccagaaat atactagagc acttcatgat tcaagtatca caggaatttc acctattaca    360

gagtatcttg cttctctaag cacatacaat gatcaatcca ttacttttgc tttggaggat    420

gaaagttatg agatatatgt tgaagacttg aaaaaagatg aaaagaaaga taaggtgtta    480

ctgagttact atgagtctca acacccctca aatgaatcag gtgacggtgt tgatggtaag    540

atgttaatgg taaccctgag tcctacaaaa gacttctggt tgcatgccaa caacaaggaa    600

cactctgtgg agctccataa gtgtgaaaaa ccactgccag accaggcctt ctttgtcctt    660

cataatatgc actccaactg tgtttcattt gaatgcaaga ctgatcctgg agtgtttata    720

ggtgtaaagg ataatcatct tgctctgatt aaagtagact cttctgagaa tttgtgtact    780

gaaaatatct tgtttaagct ctctgaaact tag                                 813


<210> SEQ ID NO 2
<211> LENGTH: 270
<212> TYPE: PRT
<213> ORGANISM: Homo sapiens

<400> SEQUENCE: 2

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270


<210> SEQ ID NO 3
```

```
<211> LENGTH: 801
<212> TYPE: DNA
<213> ORGANISM: Mus musculus

<400> SEQUENCE: 3

atgagaccta gaatgaagta ttccaactcc aagatttccc cggcaaagtt cagcagcacc     60

gcaggggaac gctcggtccc gccttgcaaa ataagaagat cccaacagaa gaccaaagaa    120

ttctgccatg tctactgcat gagactccgt tctggcctca ccataagaaa ggagactagt    180

tattttagga aagaacccac gaaaagatat tcactaaaat cgggtaccaa gcatgaagag    240

aacttctctg cctatccacg ggattctagg aagagatcct tgcttggcag tatccaagca    300

tttgctgcgt ctgttgacac attgagcatc caaggaactt cacttttaac acagtctcct    360

gcctccctga gtacatacaa tgaccaatct gttagttttg ttttggagaa tggatgttat    420

gtgatcaatg ttgacgactc tggaaaagac caagagcaag accaggtgct actacgctac    480

tatgagtctc cctgtcctgc aagtcaatca ggcgacggtg tggatgggaa gaagctgatg    540

gtgaacatga gttccatcaa agacacagac atctggctgc atgccaacga caaggactac    600

tccgtggagc ttcaaagggg tgacgtctcg cctccggaac aggccttctt cgtccttcac    660

aaaaagtcct cggactttgt ttcatttgaa tgcaagaatc ttcctggcac ttacatagga    720

gtgaaggaca accagctggc tctagtggag gaaaaagatg agagctgcaa caatattatg    780

tttaagctct cgaaaatcta a                                              801


<210> SEQ ID NO 4
<211> LENGTH: 266
<212> TYPE: PRT
<213> ORGANISM: Mus musculus

<400> SEQUENCE: 4

Met Arg Pro Arg Met Lys Tyr Ser Asn Ser Lys Ile Ser Pro Ala Lys
1               5                   10                  15

Phe Ser Ser Thr Ala Gly Glu Ala Leu Val Pro Pro Cys Lys Ile Arg
            20                  25                  30

Arg Ser Gln Gln Lys Thr Lys Glu Phe Cys His Val Tyr Cys Met Arg
        35                  40                  45

Leu Arg Ser Gly Leu Thr Ile Arg Lys Glu Thr Ser Tyr Phe Arg Lys
    50                  55                  60

Glu Pro Thr Lys Arg Tyr Ser Leu Lys Ser Gly Thr Lys His Glu Glu
65                  70                  75                  80

Asn Phe Ser Ala Tyr Pro Arg Asp Ser Arg Lys Arg Ser Leu Leu Gly
                85                  90                  95

Ser Ile Gln Ala Phe Ala Ala Ser Val Asp Thr Leu Ser Ile Gln Gly
            100                 105                 110

Thr Ser Leu Leu Thr Gln Ser Pro Ala Ser Leu Ser Thr Tyr Asn Asp
        115                 120                 125

Gln Ser Val Ser Phe Val Leu Glu Asn Gly Cys Tyr Val Ile Asn Val
    130                 135                 140

Asp Asp Ser Gly Lys Asp Gln Glu Gln Asp Gln Val Leu Leu Arg Tyr
145                 150                 155                 160

Tyr Glu Ser Pro Cys Pro Ala Ser Gln Ser Gly Asp Gly Val Asp Gly
                165                 170                 175

Lys Lys Leu Met Val Asn Met Ser Pro Ile Lys Asp Thr Asp Ile Trp
            180                 185                 190

Leu His Ala Asn Asp Lys Asp Tyr Ser Val Glu Leu Gln Arg Gly Asp
```

```
        195                 200                 205

Val Ser Pro Pro Glu Gln Ala Phe Phe Val Leu His Lys Lys Ser Ser
    210                 215                 220

Asp Phe Val Ser Phe Glu Cys Lys Asn Leu Pro Gly Thr Tyr Ile Gly
225                 230                 235                 240

Val Lys Asp Asn Gln Leu Ala Leu Val Glu Glu Lys Asp Glu Ser Cys
                245                 250                 255

Asn Asn Ile Met Phe Lys Leu Ser Lys Ile
            260                 265


<210> SEQ ID NO 5
<211> LENGTH: 1671
<212> TYPE: DNA
<213> ORGANISM: Homo sapiens

<400> SEQUENCE: 5

atggggtttt ggatcttagc aattctcaca attctcatgt attccacagc agcaaagttt      60

agtaaacaat catggggcct ggaaaatgag gctttaattg taagatgtcc tagacaagga     120

aaacctagtt acaccgtgga ttggtattac tcacaaacaa acaaaagtat tcccactcag     180

gaaagaaatc gtgtgtttgc ctcaggccaa cttctgaagt ttctaccagc tgaagttgct     240

gattctggta tttatacctg tattgtcaga agtcccacat tcaataggac tggatatgcg     300

aatgtcacca tatataaaaa acaatcagat tgcaatgttc cagattattt gatgtattca     360

acagtatctg gatcagaaaa aaattccaaa atttattgtc ctaccattga cctctacaac     420

tggacagcac ctcttgagtg gtttaagaat tgtcaggctc ttcaaggatc aaggtacagg     480

gcgcacaagt catttttggt cattgataat gtgatgactg aggacgcagg tgattacacc     540

tgtaaattta tacacaatga aaatggagcc aattatagtg tgacggcgac caggtccttc     600

acggtcaagg atgagcaagg cttttctctg tttccagtaa tcggagcccc tgcacaaaat     660

gaaataaagg aagtggaaat tggaaaaaac gcaaacctaa cttgctctgc ttgttttgga     720

aaaggcactc agttcttggc tgccgtcctg tggcagctta atggaacaaa aattacagac     780

tttggtgaac caagaattca acaagaggaa gggcaaaatc aaagtttcag caatgggctg     840

gcttgtctag acatggtttt aagaatagct gacgtgaagg aagaggattt attgctgcag     900

tacgactgtc tggccctgaa tttgcatggc ttgagaaggc acaccgtaag actaagtagg     960

aaaaatccaa ttgatcatca tagcatctac tgcataattg cagtatgtag tgtattttta    1020

atgctaatca atgtcctggt tatcatccta aaaatgttct ggattgaggc cactctgctc    1080

tggagagaca tagctaaacc ttacaagact aggaatgatg gaaagctcta tgatgcttat    1140

gttgtctacc cacggaacta caaatccagt acagatgggg ccagtcgtgt agagcacttt    1200

gttcaccaga ttctgcctga tgttcttgaa aataaatgtg gctatacctt atgcatttat    1260

gggagagata tgctacctgg agaagatgta gtcactgcag tggaaaccaa catacgaaag    1320

agcaggcggc acattttcat cctgacccct cagatcactc acaataagga gtttgcctac    1380

gagcaggagg ttgccctgca ctgtgccctc atccagaacg acgccaaggt gatacttatt    1440

gagatggagg ctctgagcga gctggacatg ctgcaggctg aggcgcttca ggactccctc    1500

cagcatctta tgaaagtaca ggggaccatc aagtggaggg aggaccacat tgccaataaa    1560

aggtccctga attccaaatt ctggaagcac gtgaggtacc aaatgcctgt gccaagcaaa    1620

attcccagaa aggcctctag tttgactccc ttggctgccc agaagcaata g             1671
```

<210> SEQ ID NO 6
<211> LENGTH: 556
<212> TYPE: PRT
<213> ORGANISM: Homo sapiens

<400> SEQUENCE: 6

```
Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Glu Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ile Ala Val Cys
                325                 330                 335

Ser Val Phe Leu Met Leu Ile Asn Val Leu Val Ile Ile Leu Lys Met
            340                 345                 350

Phe Trp Ile Glu Ala Thr Leu Leu Trp Arg Asp Ile Ala Lys Pro Tyr
        355                 360                 365

Lys Thr Arg Asn Asp Gly Lys Leu Tyr Asp Ala Tyr Val Val Tyr Pro
    370                 375                 380
```

```
Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
                405                 410                 415

Leu Cys Ile Tyr Gly Arg Asp Met Leu Pro Gly Glu Asp Val Val Thr
            420                 425                 430

Ala Val Glu Thr Asn Ile Arg Lys Ser Arg Arg His Ile Phe Ile Leu
        435                 440                 445

Thr Pro Gln Ile Thr His Asn Lys Glu Phe Ala Tyr Glu Gln Glu Val
    450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
                485                 490                 495

Gln Asp Ser Leu Gln His Leu Met Lys Val Gln Gly Thr Ile Lys Trp
            500                 505                 510

Arg Glu Asp His Ile Ala Asn Lys Arg Ser Leu Asn Ser Lys Phe Trp
        515                 520                 525

Lys His Val Arg Tyr Gln Met Pro Val Pro Ser Lys Ile Pro Arg Lys
    530                 535                 540

Ala Ser Ser Leu Thr Pro Leu Ala Ala Gln Lys Gln
545                 550                 555
```

<210> SEQ ID NO 7
<211> LENGTH: 1704
<212> TYPE: DNA
<213> ORGANISM: Mus musculus

<400> SEQUENCE: 7

```
atgattgaca gacagagaat gggactttgg gctttggcaa ttctgacact tcccatgtat     60

ttgacagtta cggagggcag taaatcgtcc tggggtctgg aaaatgaggc tttaattgtg    120

agatgccccc aaagaggacg ctcgacttat cctgtggaat ggtattactc agatacaaat    180

gaaagtattc ctactcaaaa aagaaatcgg atctttgtct caagagatcg tctgaagttt    240

ctaccagcca gagtggaaga ctctgggatt tatgcttgtg ttatcagaag ccccaacttg    300

aataagactg gatacttgaa tgtcaccata cataaaaagc cgccaagctg caatatccct    360

gattatttga tgtactcgac agtacgtgga tcagataaaa atttcaagat aacgtgtcca    420

acaattgacc tgtataattg gacagcacct gttcagtggt ttaagaactg caaagctctc    480

caagagccaa ggttcagggc acacaggtcc tacttgttca ttgacaacgt gactcatgat    540

gatgaaggtg actacacttg tcaattcaca cacgcggaga atggaaccaa ctacatcgtg    600

acggccacca gatcattcac agttgaagaa aaaggctttt ctatgtttcc agtaattaca    660

aatcctccat acaaccacac aatggaagtg gaaataggaa aaccagcaag tattgcctgt    720

tcagcttgct ttggcaaagg ctctcacttc ttggctgatg tcctgtggca gattaacaaa    780

acagtagttg gaaattttgg tgaagcaaga attcaagaag aggaaggtcg aaatgaaagt    840

tccagcaatg acatggattg tttaacctca gtgttaagga taactggtgt gacagaaaag    900

gacctgtccc tggaatatga ctgtctggcc ctgaaccttc atggcatgat aaggcacacc    960

ataaggctga gaaggaaaca accaattgat caccgaagca tctactacat agttgctgga   1020

tgtagtttat tgctaatgtt tatcaatgtc ttggtgatag tcttaaaagt gttctggatt   1080

gaggttgctc tgttctggag agatatagtg acaccttaca aaacccggaa cgatggcaag   1140
```

```
ctctacgatg cgtacatcat ttaccctcgg gtcttccggg gcagcgcggc gggaacccac   1200

tctgtggagt actttgttca ccacactctg cccgacgttc ttgaaaataa atgtggctac   1260

aaattgtgca tttatgggag agacctgtta cctgggcaag atgcagccac cgtggtggaa   1320

agcagtatcc agaatagcag aagacaggtg tttgttctgg cccctcacat gatgcacagc   1380

aaggaatttg cctacgagca ggagattgct ctgcacagcg ccctcatcca gaacaactcc   1440

aaggtgattc ttattgaaat ggagcctctg ggtgaggcaa gccgactaca ggttggggac   1500

ctgcaagatt ctctccagca tcttgtgaaa attcagggga ccatcaagtg gagggaagat   1560

catgtggccg acaagcagtc tctaagttcc aaattctgga agcatgtgag gtaccaaatg   1620

ccagtgccag aaagagcctc caagacggca tctgttgcgg ctccgttgag tggcaaggca   1680

tgcttagacc tgaaacactt ttga                                          1704
```

```
<210> SEQ ID NO 8
<211> LENGTH: 567
<212> TYPE: PRT
<213> ORGANISM: Mus musculus

<400> SEQUENCE: 8

Met Ile Asp Arg Gln Arg Met Gly Leu Trp Ala Leu Ala Ile Leu Thr
1               5                   10                  15

Leu Pro Met Tyr Leu Thr Val Thr Glu Gly Ser Lys Ser Ser Trp Gly
            20                  25                  30

Leu Glu Asn Glu Ala Leu Ile Val Arg Cys Pro Gln Arg Gly Arg Ser
        35                  40                  45

Thr Tyr Pro Val Glu Trp Tyr Tyr Ser Asp Thr Asn Glu Ser Ile Pro
    50                  55                  60

Thr Gln Lys Arg Asn Arg Ile Phe Val Ser Arg Asp Arg Leu Lys Phe
65                  70                  75                  80

Leu Pro Ala Arg Val Glu Asp Ser Gly Ile Tyr Ala Cys Val Ile Arg
                85                  90                  95

Ser Pro Asn Leu Asn Lys Thr Gly Tyr Leu Asn Val Thr Ile His Lys
            100                 105                 110

Lys Pro Pro Ser Cys Asn Ile Pro Asp Tyr Leu Met Tyr Ser Thr Val
        115                 120                 125

Arg Gly Ser Asp Lys Asn Phe Lys Ile Thr Cys Pro Thr Ile Asp Leu
    130                 135                 140

Tyr Asn Trp Thr Ala Pro Val Gln Trp Phe Lys Asn Cys Lys Ala Leu
145                 150                 155                 160

Gln Glu Pro Arg Phe Arg Ala His Arg Ser Tyr Leu Phe Ile Asp Asn
                165                 170                 175

Val Thr His Asp Asp Glu Gly Asp Tyr Thr Cys Gln Phe Thr His Ala
            180                 185                 190

Glu Asn Gly Thr Asn Tyr Ile Val Thr Ala Thr Arg Ser Phe Thr Val
        195                 200                 205

Glu Glu Lys Gly Phe Ser Met Phe Pro Val Ile Thr Asn Pro Pro Tyr
    210                 215                 220

Asn His Thr Met Glu Val Glu Ile Gly Lys Pro Ala Ser Ile Ala Cys
225                 230                 235                 240

Ser Ala Cys Phe Gly Lys Gly Ser His Phe Leu Ala Asp Val Leu Trp
                245                 250                 255

Gln Ile Asn Lys Thr Val Val Gly Asn Phe Gly Glu Ala Arg Ile Gln
            260                 265                 270
```

```
Glu Glu Glu Gly Arg Asn Glu Ser Ser Ser Asn Asp Met Asp Cys Leu
        275                 280                 285

Thr Ser Val Leu Arg Ile Thr Gly Val Thr Glu Lys Asp Leu Ser Leu
    290                 295                 300

Glu Tyr Asp Cys Leu Ala Leu Asn Leu His Gly Met Ile Arg His Thr
305                 310                 315                 320

Ile Arg Leu Arg Arg Lys Gln Pro Ile Asp His Arg Ser Ile Tyr Tyr
                325                 330                 335

Ile Val Ala Gly Cys Ser Leu Leu Leu Met Phe Ile Asn Val Leu Val
            340                 345                 350

Ile Val Leu Lys Val Phe Trp Ile Glu Val Ala Leu Phe Trp Arg Asp
        355                 360                 365

Ile Val Thr Pro Tyr Lys Thr Arg Asn Asp Gly Lys Leu Tyr Asp Ala
    370                 375                 380

Tyr Ile Ile Tyr Pro Arg Val Phe Arg Gly Ser Ala Ala Gly Thr His
385                 390                 395                 400

Ser Val Glu Tyr Phe Val His His Thr Leu Pro Asp Val Leu Glu Asn
                405                 410                 415

Lys Cys Gly Tyr Lys Leu Cys Ile Tyr Gly Arg Asp Leu Leu Pro Gly
            420                 425                 430

Gln Asp Ala Ala Thr Val Val Glu Ser Ser Ile Gln Asn Ser Arg Arg
        435                 440                 445

Gln Val Phe Val Leu Ala Pro His Met Met His Ser Lys Glu Phe Ala
    450                 455                 460

Tyr Glu Gln Glu Ile Ala Leu His Ser Ala Leu Ile Gln Asn Asn Ser
465                 470                 475                 480

Lys Val Ile Leu Ile Glu Met Glu Pro Leu Gly Glu Ala Ser Arg Leu
                485                 490                 495

Gln Val Gly Asp Leu Gln Asp Ser Leu Gln His Leu Val Lys Ile Gln
            500                 505                 510

Gly Thr Ile Lys Trp Arg Glu Asp His Val Ala Asp Lys Gln Ser Leu
        515                 520                 525

Ser Ser Lys Phe Trp Lys His Val Arg Tyr Gln Met Pro Val Pro Glu
    530                 535                 540

Arg Ala Ser Lys Thr Ala Ser Val Ala Ala Pro Leu Ser Gly Lys Ala
545                 550                 555                 560

Cys Leu Asp Leu Lys His Phe
                565
```

<210> SEQ ID NO 9
<211> LENGTH: 1233
<212> TYPE: DNA
<213> ORGANISM: Homo sapiens

<400> SEQUENCE: 9

```
atgccaggtg tctgtgatag ggcccctgac ttcctctccc cgtctgaaga ccaggtgctg     60

aggcctgcct tgggcagctc agtggctctg aactgcacgg cttgggtagt ctctgggccc    120

cactgctccc tgccttcagt ccagtggctg aaagacgggc ttccattggg aattgggggc    180

cactacagcc tccacgagta ctcctgggtc aaggccaacc tgtcagaggt gcttgtgtcc    240

agtgtcctgg gggtcaacgt gaccagcact gaagtctatg gggccttcac ctgctccatc    300

cagaacatca gcttctcctc cttcactctt cagagagctg gccctacaag ccacgtggct    360

gcggtgctgg cctccctcct ggtcctgctg gccctgctgc tggccgccct gctctatgtc    420
```

```
aagtgccgtc tcaacgtgct gctctggtac caggacgcgt atggggaggt ggagataaac    480

gacgggaagc tctacgacgc ctacgtctcc tacagcgact gccccgagga ccgcaagttc    540

gtgaacttca tcctaaagcc gcagctggag cggcgtcggg gctacaagct cttcctggac    600

gaccgcgacc tcctgccgcg cgctgagccc tccgccgacc tcttggtgaa cctgagccgc    660

tgccgacgcc tcatcgtggt gctttcggac gccttcctga gccgggcctg gtgcagccac    720

agcttccggg agggcctgtg ccggctgctg gagctcaccc gcagacccat cttcatcacc    780

ttcgagggcc agaggcgcga ccccgcgcac ccggcgctcc gcctgctgcg ccagcaccgc    840

cacctggtga ccttgctgct ctggaggccc ggctccgtga ctccttcctc cgatttttgg    900

aaagaagtgc agctggcgct gccgcggaag gtgcggtaca ggccggtgga aggagacccc    960

cagacgcagc tgcaggacga caaggacccc atgctgattc ttcgaggccg agtccctgag   1020

ggccgggccc tggactcaga ggtggacccg gaccctgagg gcgacctggg tgtccggggg   1080

cctgtttttg gagagccatc agctccaccg cacaccagtg ggtctcgct gggagagagc   1140

cggagcagcg aagtggacgt ctcggatctc ggctcgcgaa actacagtgc ccgcacagac   1200

ttctactgcc tggtgtccaa ggatgatatg tag                                1233
```

<210> SEQ ID NO 10
<211> LENGTH: 410
<212> TYPE: PRT
<213> ORGANISM: Homo sapiens

<400> SEQUENCE: 10

```
Met Pro Gly Val Cys Asp Arg Ala Pro Asp Phe Leu Ser Pro Ser Glu
1               5                   10                  15

Asp Gln Val Leu Arg Pro Ala Leu Gly Ser Ser Val Ala Leu Asn Cys
            20                  25                  30

Thr Ala Trp Val Val Ser Gly Pro His Cys Ser Leu Pro Ser Val Gln
        35                  40                  45

Trp Leu Lys Asp Gly Leu Pro Leu Gly Ile Gly Gly His Tyr Ser Leu
    50                  55                  60

His Glu Tyr Ser Trp Val Lys Ala Asn Leu Ser Glu Val Leu Val Ser
65                  70                  75                  80

Ser Val Leu Gly Val Asn Val Thr Ser Thr Glu Val Tyr Gly Ala Phe
                85                  90                  95

Thr Cys Ser Ile Gln Asn Ile Ser Phe Ser Ser Phe Thr Leu Gln Arg
            100                 105                 110

Ala Gly Pro Thr Ser His Val Ala Ala Val Leu Ala Ser Leu Leu Val
        115                 120                 125

Leu Leu Ala Leu Leu Leu Ala Ala Leu Leu Tyr Val Lys Cys Arg Leu
    130                 135                 140

Asn Val Leu Leu Trp Tyr Gln Asp Ala Tyr Gly Glu Val Glu Ile Asn
145                 150                 155                 160

Asp Gly Lys Leu Tyr Asp Ala Tyr Val Ser Tyr Ser Asp Cys Pro Glu
                165                 170                 175

Asp Arg Lys Phe Val Asn Phe Ile Leu Lys Pro Gln Leu Glu Arg Arg
            180                 185                 190

Arg Gly Tyr Lys Leu Phe Leu Asp Asp Arg Asp Leu Leu Pro Arg Ala
        195                 200                 205

Glu Pro Ser Ala Asp Leu Leu Val Asn Leu Ser Arg Cys Arg Arg Leu
    210                 215                 220

Ile Val Val Leu Ser Asp Ala Phe Leu Ser Arg Ala Trp Cys Ser His
```

-continued

```
225                 230                 235                 240

Ser Phe Arg Glu Gly Leu Cys Arg Leu Leu Glu Leu Thr Arg Arg Pro
                245                 250                 255

Ile Phe Ile Thr Phe Glu Gly Gln Arg Arg Asp Pro Ala His Pro Ala
            260                 265                 270

Leu Arg Leu Leu Arg Gln His Arg His Leu Val Thr Leu Leu Leu Trp
        275                 280                 285

Arg Pro Gly Ser Val Thr Pro Ser Ser Asp Phe Trp Lys Glu Val Gln
    290                 295                 300

Leu Ala Leu Pro Arg Lys Val Arg Tyr Arg Pro Val Glu Gly Asp Pro
305                 310                 315                 320

Gln Thr Gln Leu Gln Asp Asp Lys Asp Pro Met Leu Ile Leu Arg Gly
                325                 330                 335

Arg Val Pro Glu Gly Arg Ala Leu Asp Ser Glu Val Asp Pro Asp Pro
            340                 345                 350

Glu Gly Asp Leu Gly Val Arg Gly Pro Val Phe Gly Glu Pro Ser Ala
        355                 360                 365

Pro Pro His Thr Ser Gly Val Ser Leu Gly Glu Ser Arg Ser Ser Glu
    370                 375                 380

Val Asp Val Ser Asp Leu Gly Ser Arg Asn Tyr Ser Ala Arg Thr Asp
385                 390                 395                 400

Phe Tyr Cys Leu Val Ser Lys Asp Asp Met
                405                 410
```

<210> SEQ ID NO 11
<211> LENGTH: 1229
<212> TYPE: DNA
<213> ORGANISM: Mus musculus

<400> SEQUENCE: 11

```
atggcaggtg tctgtgacat ggcccctaat ttcctttccc catctgaaga ccaggccttg     60

ggtcttgccc ttggcagaga agttgctttg aattgcacag cttgggtgtt ctctaggccc    120

cagtgtcccc agccatcagt gcagtggctg aaagatggtc tggcattggg caatggaagc    180

cacttcagcc tccatgagga cttctgggtc agcgccaact tctcagagat tgtgtccagt    240

gtcctggtgc tcaacttgac caatgcagag gactatggaa ccttcacctg ttctgtctgg    300

aatgtcagct cccattcctt cactctttgg cgagctggcc ctgctggcca tgtggctgca    360

gtactggctt ccctcctggt cctggtggtt ctgctgctgg tggccctgct ctatgttaag    420

tgtcggctga acatgctgct ttggtaccaa gacacttacg gggaggtgga gatgaacgat    480

gggaagttat acgatgccta cgtgtcctat agcgactgcc cagaggaccg caaatttgta    540

aattttattc tgaagcctca gttggagcgg cgtcggggat acaaactctt cctagaggac    600

cgcgacctct tgcctcgcgc ggagccctct gccgaccttt tggtgaacct gagtcgctgt    660

cggcgtctca tcgtggttct ttcagatgcc ttcctaagcc ggccctggtg tagccagagc    720

ttccgggagg gactgtgccg cctactggag ctcacccgca gacctatctt catcaccttt    780

gagggccaga ggcgtgagcc catacaccct gctctccggc tcctgcgcca gcaccgccac    840

ctcgtgaccc tggtgctttg gaagcctggc tccgtgactc cttcctctga tttttggaaa    900

gagctacagc tagcactgcc acgaaggtgc agtacaggcc ggtggaggga gaccctcaaa    960

cccgacttca ggatgacaaa gatcccatgc taatcgtgag aggacgtgct gcccagggcc   1020

ggggcatgga gtcagagctg gatccagacc ctgagggaga cctgggtgtc cgtggacctg   1080
```

```
tctttgggga gccaccaact ccactgcagg aaaccaggat ctgcatagga gagagccacg   1140

gcagtgaaat ggatgtctct gacctcggct ctcgaaacta cagtgcacgg acagacttct   1200

actgcctcgt gtctgaggat gatgtgtag                                     1229


<210> SEQ ID NO 12
<211> LENGTH: 409
<212> TYPE: PRT
<213> ORGANISM: Mus musculus

<400> SEQUENCE: 12

Met Ala Gly Val Cys Asp Met Ala Pro Asn Phe Leu Ser Pro Ser Glu
1               5                   10                  15

Asp Gln Ala Leu Gly Leu Ala Leu Gly Arg Glu Val Ala Leu Asn Cys
            20                  25                  30

Thr Ala Trp Val Phe Ser Arg Pro Gln Cys Pro Gln Pro Ser Val Gln
        35                  40                  45

Trp Leu Lys Asp Gly Leu Ala Leu Gly Asn Gly Ser His Phe Ser Leu
    50                  55                  60

His Glu Asp Phe Trp Val Ser Ala Asn Phe Ser Glu Ile Val Ser Ser
65                  70                  75                  80

Val Leu Val Leu Asn Leu Thr Asn Ala Glu Asp Tyr Gly Thr Phe Thr
                85                  90                  95

Cys Ser Val Trp Asn Val Ser Ser His Ser Phe Thr Leu Trp Arg Ala
            100                 105                 110

Gly Pro Ala Gly His Val Ala Ala Val Leu Ala Ser Leu Leu Val Leu
        115                 120                 125

Val Val Leu Leu Leu Val Ala Leu Leu Tyr Val Lys Cys Arg Leu Asn
    130                 135                 140

Met Leu Leu Trp Tyr Gln Asp Thr Tyr Gly Glu Val Glu Met Asn Asp
145                 150                 155                 160

Gly Lys Leu Tyr Asp Ala Tyr Val Ser Tyr Ser Asp Cys Pro Glu Asp
                165                 170                 175

Arg Lys Phe Val Asn Phe Ile Leu Lys Pro Gln Leu Glu Arg Arg Arg
            180                 185                 190

Gly Tyr Lys Leu Phe Leu Glu Asp Arg Asp Leu Leu Pro Arg Ala Glu
        195                 200                 205

Pro Ser Ala Asp Leu Leu Val Asn Leu Ser Arg Cys Arg Arg Leu Ile
    210                 215                 220

Val Val Leu Ser Asp Ala Phe Leu Ser Arg Pro Trp Cys Ser Gln Ser
225                 230                 235                 240

Phe Arg Glu Gly Leu Cys Arg Leu Leu Glu Leu Thr Arg Arg Pro Ile
                245                 250                 255

Phe Ile Thr Phe Glu Gly Gln Arg Arg Glu Pro Ile His Pro Ala Leu
            260                 265                 270

Arg Leu Leu Arg Gln His Arg His Leu Val Thr Leu Val Leu Trp Lys
        275                 280                 285

Pro Gly Ser Val Thr Pro Ser Ser Asp Phe Trp Lys Glu Leu Gln Leu
    290                 295                 300

Ala Leu Pro Arg Lys Val Gln Tyr Arg Pro Val Glu Gly Asp Pro Gln
305                 310                 315                 320

Thr Arg Leu Gln Asp Asp Lys Asp Pro Met Leu Ile Val Arg Gly Arg
                325                 330                 335

Ala Ala Gln Gly Arg Gly Met Glu Ser Glu Leu Asp Pro Asp Pro Glu
            340                 345                 350
```

```
Gly Asp Leu Gly Val Arg Gly Pro Val Phe Gly Glu Pro Pro Thr Pro
        355                 360                 365

Leu Gln Glu Thr Arg Ile Cys Ile Gly Glu Ser His Gly Ser Glu Met
    370                 375                 380

Asp Val Ser Asp Leu Gly Ser Arg Asn Tyr Ser Ala Arg Thr Asp Phe
385                 390                 395                 400

Tyr Cys Leu Val Ser Glu Asp Asp Val
                405
```

METHODS OF MODULATING CYTOKINE ACTIVITY; RELATED REAGENTS

This filing is a Continuation of co-pending U.S. patent application Ser. No. 12/239,689, filed Sep. 26, 2008, which is a Continuation of U.S. patent application Ser. No. 11/682,224, filed Mar. 5, 2007, which is a Continuation of U.S. patent application Ser. No. 11/059,117, filed Feb. 15, 2005, which claims benefit of U.S. Provisional Patent Application No. 60/545,730, filed Feb. 17, 2004, each of which is incorporated herein by reference.

The Sequence Listing filed electronically herewith is also hereby incorporated by reference in its entirety (File Name: DX06173USCNT-SEQLIST-03FEB2014.txt; Date Created: Feb. 3, 2014; File Size: 31.2 KB.)

FIELD OF THE INVENTION

The present invention relates generally to uses of mammalian cytokines. More specifically, the invention discloses methods of using IL-33, and a receptor for IL-33.

BACKGROUND OF THE INVENTION

The immune system protects individuals from infective agents, e.g., bacteria, multi-cellular organisms, as well as cancers. This system includes several types of lymphoid and myeloid cells such as monocytes, macrophages, dendritic cells (DCs), eosinophils, T cells, B cells, and neutrophils. These lymphoid and myeloid cells often produce signaling proteins known as cytokines. Immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Immune response sometimes results in pathological consequences, that is, inflammatory disorders. These inflammatory disorders, which involve immune cells and cytokines, include, e.g., psoriasis, rheumatoid arthritis, Crohn's disease, multiple sclerosis, and atherosclerosis (see, e.g., Abbas, et al. (eds.) (2000) *Cellular and Molecular Immunology*, W.B. Saunders Co., Philadelphia, Pa.; Oppenheim and Feldmann (eds.) (2001) *Cytokine Reference*, Academic Press, San Diego, Calif.; Kaufmann, et al. (2001) *Immunobiol.* 204:603-613; Saurez and Schultz-Cheery (2000) *Dev. Comp. Immunol.* 24:269-283; van Reeth and Nauwynck (2000) *Vet. Res.* 31:187-213; Garcia-Sastre (2001) *Virology* 279:375-384; Katze, et al. (2002) *Nat. Rev. Immunol.* 2:675-687; van Reeth (2000) *Vet. Microbiol.* 74:109-116; Tripp (2003) *Curr. Pharm. Des.* 9:51-59).

The interleukin-1 (IL-1) family of cytokines contributes to the pathology of inflammatory disorders and proliferative conditions, e.g., arthritis and cancer. Cytokines of the IL-1 family include IL-1alpha, IL-1beta, IL-1delta, IL-1epsilon, basic fibroblast growth factor, IL-18, CREG and CREG2. IL-1alpha and IL-1beta are biosynthesized as 31 kDa polypeptides that are further processed to mature 17 kDa forms, while IL-1delta and IL-1epsilon appear not to possess a distinct pro-form (see, e.g., Debets, et al. (2001) *J. Immunol.* 167:1440-1446; McMahon, et al. (1997) *J. Biol. Chem.* 272:28202-28205; Irikura, et al. (2002) *New Engl. J. Med.* 169:393-398; Kim, et al. (2002) *J. Biol. Chem.* 277:10998-11003).

The IL-1 family also includes IL-1 receptors, i.e., IL-1RI, IL-1RII, and IL-1R accessory protein (a.k.a. IL-1R1, IL-1R2, and IL-1R3, respectively). IL-1alpha and IL-1beta trigger cell signaling by binding to IL-1R1, while IL-1RII can function as a molecule that absorbs circulating ligand. IL-1 receptor antagonist (IL-1Ra), another IL-1 family protein, binds to IL-1 receptor without transmitting a signal and serves as an inhibitor of IL-1. IL-1ra and IL-1delta play similar roles in antagonizing signaling through receptors, i.e., IL-1ra antagonizes IL-1alpha-mediated signaling via IL-1R1, while IL-1delta antagonizes IL-1epsilon-mediated signaling via IL-1R6 (see, e.g., You, et al. (2001) *New Engl. J. Med.* 193:101-109). Debets, et al. (2001) J. Immunol. 167:1440-1446; Apte and Voronov (2002) *Sem. Cancer Biol.* 12:277-290; Wong, et al. (1997) *Proc. Natl. Acad. Sci. USA* 94:227-232).

IL-1 family members play a role in inflammatory conditions, e.g., rheumatoid arthritis, psoriasis, asthma, chronic obstructive pulmonary disorder (COPD), sepsis, and inflammatory bowel disorder (IBD). Rheumatoid arthritis (RA) is a common chronic inflammatory disorder characterized by degradation of joints, e.g., the synovial membrane, cartilage, and bone. The disorder strikes about 1% of the population and cannot be cured. IL-1 stimulates a number of cells involved in arthritic inflammation, e.g., fibroblasts, osteoclasts, chondrocytes, and neutrophils, which may show abnormal proliferation and release enzymes causing joint destruction (see, e.g., (Debets, et al. (1997) *J. Immunol.* 158:2955-2963; Lacey, et al. (2003) *Arthritis Rheum.* 48: 103-109; Chung (2001) *Eur. Resp. J. Suppl.* 34: 50s-59s; Freeman and Buchman (2001) *Expert Opin. Biol. Ther.* 1:301-308; Dinarello (2000) *Chest* 118:503-508). Krause, et al. (2002) *J. Immunol.* 169:6610-6616; Choy and Panayi (2001) *New Engl. J. Med.* 344:907-916; Woolley (2003) *New Engl. J. Med.* 348:1709-1711; Williams, et al. (2000) *New Engl. J. Med.* 164: 7240-7245; Feldmann and Maini (2001) *Annu. Rev. Immunol.* 19:163-196; Lacey, et al., supra; Niki, et al. (2001) *J. Clin. Invest.* 107:1127-1135; Attur, et al. (2000) *J. Biol. Chem.* 51:40307-40315).

Proliferative disorders are the second most common cause of death in the United States (Anderson (2002) National Vital Statistics Reports 50:1-86; Toribara and Sleisenger (2003) *New Engl. J. Med.* 332:861-867; Janne and Mayer (2000) *New Engl. J. Med.* 342:1960-1968; Fuchs and Mayer (1995) *New Engl. J. Med.* 333:32-41). Cytokines of the IL-1 family have been implicated in the control and pathology of proliferative disorders, i.e., cancer. IL-1 modulates progression through the cell cycle, e.g., by changing expression of cyclin-dependent kinases and cyclin-dependent kinase inhibitors. High doses of IL-1beta promote tumor invasiveness, while low doses can promote immune eradication of tumors (see, e.g., Zeisler, et al. (1998) *Eur. J. Cancer* 34:931-933; Yoshida, et al. (2002) *Brit. J. Cancer* 86:1396-1400; Nesbit, et al. (1999) *Oncogene* 18:6469-6476; Dinarello, et al. (1998) *J. Leuko. Biol.* 63:658-664; Apte and Voronov, supra; Saijo, et al. (2002) *New Engl. J. Med.* 169: 469-475; Murai, et al. (2001) *J. Biol. Chem.* 276:6797-6806; Koudssi, et al. (1998) *J. Biol. Chem.* 273: 25796-25803; Zeki, et al. (1999) *J. Endocrinol.* 160:67-73; Osawa, et al. (2000) *J. Biochem.* 127:883-893).

There is an unmet need to treat inflammatory and immune disorders. The present invention fulfils this need by providing methods of using agonists and antagonists of IL-33 or IL-33 receptor.

SUMMARY OF THE INVENTION

The present invention is based, in part, upon the discovery that an agonist or antagonist of IL-33 or IL-33 receptor (previously known as IL-100 and IL-100 receptor) modulates response to a number of immune and inflammatory conditions.

The present invention provides a method of modulating an immune disorder or condition, comprising administering an effective amount of an agonist or antagonist of IL-33 or IL-33R complex. Also provided is the above method wherein the disorder or condition comprises: a) innate response; b) asthma or allergy; c) multiple sclerosis; d) an inflammatory bowel disorder; e) arthritis; f) infection; g) a cancer or tumor. Further provided is the above method wherein the infection comprises: a) an intracellular pathogen; b) a bacterium; c) a parasite; or d) a virus; and the above method wherein the intracellular pathogen is: a) *Leishmania* sp.; b) *Mycobacterium* sp.; c) *Listeria* sp.; d) *Toxoplasma* sp.; e) *Schistosoma*; or f) a respiratory virus. Moreover, the present invention provides the above method wherein the immune disorder or conditions comprises TH1-type response or TH2-type response; and the above method wherein the TH2-type response comprises an early event in TH2-type response; as well as the above method wherein the arthritis comprises rheumatoid arthritis; osteoarthritis; or psoriatic arthritis.

In another embodiment, the present invention provides the above method wherein the agonist comprises IL-33 or a nucleic acid; as well as the above method wherein the nucleic acid encodes IL-33; and the above method wherein the antagonist comprises a binding composition from an antibody that specifically binds IL-33 or a complex of IL-33, T1/ST2 and SIGIRR (IL-33R). In yet another embodiment, the present invention provides the above method wherein the binding composition from an antibody comprises a polyclonal antibody; a monoclonal antibody; a humanized antibody, or a fragment thereof; an Fab, Fv, or $F(ab')_2$ fragment; a peptide mimetic of an antibody; or a detectable label. Also provided is the above method, wherein the antagonist comprises: a) a soluble IL-33R; b) a small molecule; or c) a nucleic acid; and the above method wherein the nucleic acid specifically hybridizes with a polynucleotide encoding IL-33; as well as the above method wherein the nucleic acid comprises anti-sense nucleic acid or small interference RNA (siRNA).

In another aspect, the present invention provides a method of modulating blood cell counts comprising administering an effective amount of an agonist or antagonist of IL-33; and the above method wherein the IL-33 agonist increases the counts of total white blood cells; neutrophils; lymphocytes; or eosinophils; as well as the above method wherein the IL-33 antagonist increases the count of platelets; and the above method wherein the IL-33 antagonist decreases the counts of total white blood cells; neutrophils; lymphocytes; or eosinophils.

Yet another aspect of the present invention provides a method of diagnosing the immune condition or disorder noted above, comprising contacting a binding composition to a biological sample, wherein the binding composition specifically binds to IL-33, and measuring or determining the specific binding of the binding composition to the biological sample. Also provided is a kit for the diagnosis of the immune condition or disorder of claim 1, comprising a compartment and a binding composition that specifically binds to: IL-33; an IL-33R complex; a complex of IL-33 and IL-33R; or a nucleic acid encoding IL-33.

DETAILED DESCRIPTION OF THE PREFERRED EMBODIMENTS

Figure 1:
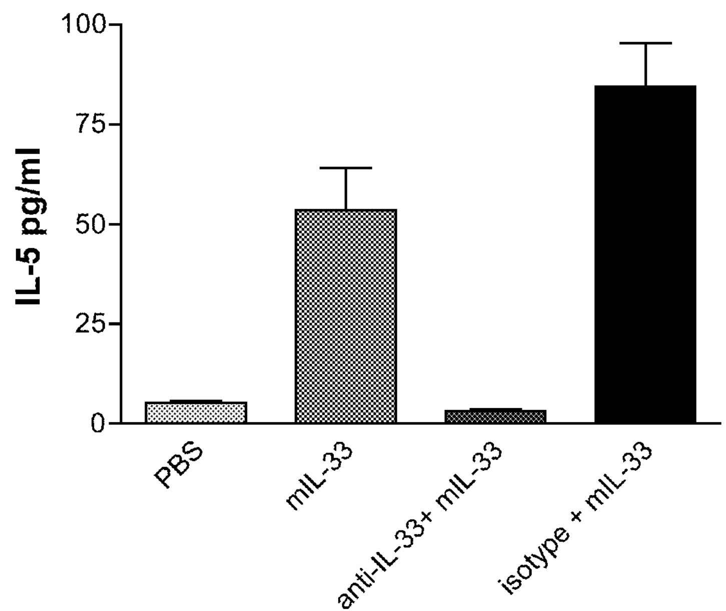
FIG. 1 shows IL-5 production in IL-33+anti-IL-33 antibody treated mice versus IL-33 alone and isotype control antibody treated mice.

As used herein, including the appended claims, the singular forms of words such as “a,” “an,” and “the,” include their corresponding plural references unless the context clearly dictates otherwise.

All references cited herein are incorporated herein by reference to the same extent as if each individual publication or patent application was specifically and individually indicated to be incorporated by reference.

I. DEFINITIONS

“Activation,” “stimulation,” and “treatment,” as it applies to cells or to receptors, may have the same meaning, e.g., activation, stimulation, or treatment of a cell or receptor with a ligand, unless indicated otherwise by the context or explicitly. “Ligand” encompasses natural and synthetic ligands, e.g., cytokines, cytokine variants, analogues, muteins, and binding compositions derived from antibodies. “Ligand” also encompasses small molecules, e.g., peptide mimetics of cytokines and peptide mimetics of antibodies. “Activation” can refer to cell activation as regulated by internal mechanisms as well as by external or environmental factors. “Response,” e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

“Activity” of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. “Activity” of a molecule may also refer to activity in modulating or maintaining cell-to-cell interactions, e.g., adhesion, or activity in maintaining a structure of a cell, e.g., cell membranes or cytoskeleton. “Activity” can also mean specific activity, e.g., [catalytic activity]/[mg protein], or [immunological activity]/[mg protein], concentration in a biological compartment, or the like. “Proliferative activity” encompasses an activity that promotes, that is necessary for, or that is specifically associated with, e.g., normal cell division, as well as cancer, tumors, dysplasia, cell transformation, metastasis, and angiogenesis.

“Administration” and “treatment,” as it applies to the administration of an agonist or antagonist of IL-33, e.g., to an animal, human, experimental subject, cell, tissue, organ, or biological fluid, refers to contact of an exogenous pharmaceutical, therapeutic, diagnostic agent, compound, or composition to the animal, human, subject, cell, tissue, organ, or biological fluid. “Administration” and “treatment” can refer, e.g., to therapeutic, placebo, pharmacokinetic, diagnostic, research, and experimental methods. "Treatment of a cell" encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an IL-33 agonist or IL-33 antagonist to a human or animal subject, a cell, tissue, physiological compartment, or physiological fluid. "Treatment of a cell" also encompasses situations where the IL-33 agonist or IL-33 antagonist contacts IL-33 receptor (T1/ST2), e.g., in the fluid phase or colloidal phase, as well as situations where the agonist or antagonist contacts a fluid, e.g., where the fluid is in contact with a cell or receptor, but where it has not been demonstrated that the agonist or antagonist contacts the cell or receptor.

"Binding composition" refers to a molecule, small molecule, macromolecule, antibody, a fragment or analogue thereof, or soluble receptor, capable of binding to a target, where the target is, e.g., IL-33 or IL-33R. "Binding composition" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, which is capable of binding to a target. "Binding composition" may also refer to a molecule in combination with a stabilizer, excipient, salt, buffer, solvent, or additive, capable of binding to a target. "Binding" may be defined as an association of the binding composition with a target where the association results in reduction in the normal Brownian motion of the binding composition, in cases where the binding composition can be dissolved or suspended in solution.

"Conservatively modified variants" applies to both amino acid and nucleic acid sequences. With respect to particular nucleic acid sequences, conservatively modified variants refers to those nucleic acids which encode identical or essentially identical amino acid sequences or, where the nucleic acid does not encode an amino acid sequence, to essentially identical nucleic acid sequences. Because of the degeneracy of the genetic code, a large number of functionally identical nucleic acids may encode any given protein. As to amino acid sequences, one of skill will recognize that an individual substitution to a nucleic acid, peptide, polypeptide, or protein sequence which substitutes an amino acid or a small percentage of amino acids in the encoded sequence for a conserved amino acid is a "conservatively modified variant." Conservative substitution tables providing functionally similar amino acids are well known in the art. An example of a conservative substitution is the exchange of an amino acid in one of the following groups for another amino acid of the same group (U.S. Pat. No. 5,767,063 issued to Lee, et al.; Kyte and Doolittle (1982) *J. Mol. Biol.* 157: 105-132):

(1) Hydrophobic: Norleucine, Ile, Val, Leu, Phe, Cys, or Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Tip, Tyr, Phe;
(7) Small amino acids: Gly, Ala, Ser.

"Derived" can be used to describe, e.g., deriving the structure of a peptide, oligopeptide, or polypeptide from a parent peptide, oligopeptide, or polypeptide, such as an antibody. In this context, derived encompasses, e.g., peptide structures where the peptide has the same sequence as a sequence found within the parent, e.g., where the peptide is identical to the parent but with a truncation at the N-terminus, C-terminus, or both N- and C-termini of the parent, or with a truncation and a fusion, or with a fusion only. Derived also means that the peptide has the same sequence as found in the parent, but with conservative amino acid changes, or with deletions or insertions, where the deletions or insertions preserve a biological property in the peptide that is inherent in the parent. "Derived" encompasses situations where the peptide or polypeptide is synthesized using the parent as a starting compound, and where the peptide or polypeptide is synthesized de novo, using the structure of the parent as a guide.

"Effective amount" or "therapeutically effective amount," of the agonist or antagonist of the IL-33 of the present invention, means an amount sufficient to ameliorate a symptom or sign of a disorder or physiological condition or an amount sufficient to permit or facilitate a diagnosis of the disorder or physiological condition. An effective amount for a particular patient or veterinary subject may vary depending on factors such as the condition being treated, the overall health of the patient, the method route and dose of administration and the severity of side affects (see, e.g., U.S. Pat. No. 5,888,530 issued to Netti, et al.). An effective amount can be the maximal dose or dosing protocol that avoids significant side effects or toxic effects. The effect will result in an improvement of a diagnostic measure, parameter, or detectable signal by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

"Exogenous" refers to substances that are produced outside an organism, cell, or human body, depending on the context. "Endogenous" refers to substances that are produced within a cell, organism, or human body, depending on the context.

"Disorder" refers to a pathological state, or a condition that is correlated with or predisposes to a pathological state. "Infectious disorder" refers, e.g., to a disorder resulting from a microbe, bacterium, parasite, virus, and the like, as well as to an inappropriate, ineffective, or pathological immune response to the disorder. "Oncogenic disorder" encompasses a cancer, transformed cell, tumor, displasia, angiogenesis, metastasis, and the like, as well as to an inappropriate, ineffective, or pathological immune response to the disorder.

"Effective amount" means, e.g., an amount of an IL-33 agonist, IL-33 antagonist, binding compound or binding composition, sufficient to ameliorate a symptom or sign of a disorder, condition, or pathological state. "Effective amount" also relates to an amount of an IL-33 agonist, antagonist, or binding compound or composition, sufficient to allow or facilitate the diagnosis of a symptom or sign of a disorder, condition, or pathological state.

"Inhibitors" and "antagonists" or "activators" and "agonists" refer to inhibitory or activating molecules, respectively, e.g., for the activation of, e.g., a ligand, receptor, cofactor, a gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule. Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a composition that reduces, blocks, or inactivates a constitutive activity. An "agonist" is a compound that interacts with a target to cause or promote an increase in the activation of the target. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activator or inhibitor and are compared to control samples without the inhibitor. Control samples, i.e., not treated with antagonist, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Expression" refers to a measure of mRNA or polypeptide encoded by a specific gene. Units of expression may be a measure of, e.g., the number of molecules of mRNA or polypeptide/mg protein, the number of molecules of mRNA or polypeptide/cell, in measurements of expression by cell, tissue, cell extract, or tissue extract. The units of expression may be relative, e.g., a comparison of signal from control and experimental mammals or a comparison of signals with a reagent that is specific for the mRNA or polypeptide versus with a reagent that is non-specific.

"Hybridization" that is specific or selective typically occurs when there is at least about 55% homology over a stretch of at least about 30 nucleotides, preferably at least about 75% over a stretch of about 25 nucleotides, and most preferably at least about 90% over about 20 nucleotides (see, e.g., Kanehisa (1984) *Nucleic Acids Res.* 12:203-213). Hybridization under stringent conditions, e.g., of a first nucleic acid to a second nucleic acid, are those that: (1) Employ low ionic strength and high temperature for washing, for example, 0.015 M sodium chloride/0.0015 M sodium citrate/0.1% sodium dodecyl sulfate at 50° C.; (2) Employ during hybridization a denaturing agent, such as formamide, for example, 50% (vol/vol) formamide with 0.1% bovine serum albumin/0.1% Ficoll® (Sigma-Aldrich, St. Louis, Mo.)/0.1% polyvinylpyrrolidone/50 mM sodium phosphate buffer at pH 6.5 with 750 mM sodium chloride, 75 mM sodium citrate at 42° C.; (3) Employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 ng/ml), 0.1% SDS, and 10% dextran sulfate at 42° C., with washes at 42° C. in 0.2×SSC and 0.1% SDS; or (4) Employ a buffer of 10% dextran sulfate, 2×SSC (sodium chloride/sodium citrate), and 50% formamide at 55° C., followed by a high-stringency wash consisting of 0.1×SSC containing EDTA at 55° C. (U.S. Pat. No. 6,387,657 issued to Botstein, et al.).

Stringent conditions for hybridization of nucleic acids are a function of salt, temperature, organic solvents, and chaotropic agents. Stringent temperature conditions will usually include temperatures in excess of about 30° C., more usually in excess of about 37° C., typically in excess of about 45° C., more typically in excess of about 50° C., preferably in excess of about 65° C., and more preferably in excess of about 70° C. Stringent salt conditions will ordinarily be less than about 1 M, more ordinarily less than about 500 mM, usually less than about 400 mM, more usually less than about 300 mM, typically less than about 200 mM, preferably less than about 100 mM, and more preferably less than about 80 mM, even down to less than about 20 mM. However, the combination of parameters is more important than the measure of any single parameter (Wetmur and Davidson (1968) *J. Mol. Biol.* 31:349-370).

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist irradication by the immune system. "Cancerous condition" includes, e.g., cancer, cancer cells, tumors, angiogenesis, and precancerous conditions such as dysplasia.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

"Inflammatory disorder" means a disorder or pathological condition where the pathology results, in whole or in part, from an increase in the number and/or increase in activation of cells of the immune system, e.g., of T cells, B cells, monocytes or macrophages, alveolar macrophages, dendritic cells, NK cells, NKT cells, neutrophils, eosinophils, or mast cells.

"IL-33 Receptor", "IL-33R", or "IL-33R complex" as used herein shall mean the association of two IL-1R family members, T1/ST2 and SIGIRR to form receptor complex responsive to stimulation with IL-33.

"Ligand" refers, e.g., to a small molecule, peptide, polypeptide, and membrane associated or membrane-bound molecule, or complex thereof, that can act as an agonist or antagonist of a receptor. "Ligand" also encompasses an agent that is not an agonist or antagonist, but that can bind to the receptor without significantly influencing its biological properties, e.g., signaling or adhesion. Moreover, "ligand" includes a membrane-bound ligand that has been changed, e.g., by chemical or recombinant methods, to a soluble version of the membrane-bound ligand. By convention, where a ligand is membrane-bound on a first cell, the receptor usually occurs on a second cell. The second cell may have the same or a different identity as the first cell. A ligand or receptor may be entirely intracellular, that is, it may reside in the cytosol, nucleus, or some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

A "first polypeptide chain" and a "second polypeptide chain" refers to two polypeptide chains not linked together by way of a classical peptide bond. Typically, the first polypeptide chain comprises an N-terminus and C-terminus, and the second polypeptide chain comprises another N-terminus and another C-terminus, that is, altogether there are two N-termini and two C-termini. The first polypeptide chain can be encoded by a first vector, while the second polypeptide chain can be encoded by a second vector. The first polypeptide chain and second polypeptide chain can be encoded by one vector, where a first promoter can be operably linked with the first polypeptide chain and a second promoter can be operably linked with the second polypeptide chain or, in another embodiment, expression of both the first and second polypeptide chains can be operably linked to the same promoter.

"Sensitivity," e.g., sensitivity of receptor to a ligand, means that binding of a ligand to the receptor results in a detectable change in the receptor, or in events or molecules specifically associated with the receptor, e.g., conformational change, phosphorylation, nature or quantity of proteins associated with the receptor, or change in genetic expression mediated by or associated with the receptor.

"Small molecules" are provided for the treatment of physiology and disorders of tumors and cancers. "Small molecule" is defined as a molecule with a molecular weight that is less than 10 kD, typically less than 2 kD, and preferably less than 1 kD. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described (see, e.g., Casset, et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos, et al. (2002) *Curr. Med. Chem.* 9:411-420; Monfardini, et al. (2002) *Curr. Pharm. Des.* 8:2185-2199; Domingues, et al. (1999) *Nat. Struct. Biol.* 6:652-656; Sato and Sone (2003) *Biochem. J.* 371:603-608; U.S. Pat. No. 6,326,482 issued to Stewart, et al).

"Soluble receptor" refers to receptors that are water-soluble and occur, e.g., in extracellular fluids, intracellular fluids, or weakly associated with a membrane. Soluble receptor further refers to receptors that are engineered to be water soluble. For T1/ST2, the soluble or extracellular domain is defined as residues 1-337 of SEQ ID NO: 6 (human) and residues 1-342 of SEQ ID NO: 8 (mouse). For SIGIRR, the soluble or extracellular domain is defined as residues 1-118 of SEQ ID NO: 10 (human) and residues 1-117 of SEQ ID NO: 12 (mouse).

"Specificity of binding," "selectivity of binding," and the like, refer to a binding interaction between a predetermined ligand and a predetermined receptor that enables one to distinguish between the predetermined ligand and other ligands, or between the predetermined receptor and other receptors. "Specifically" or "selectively" binds, when referring to a ligand/receptor, antibody/antigen, or other binding pair, indicates a binding reaction that is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, binds to its antigen with an affinity that is at least two fold greater, preferably at least ten times greater, more preferably at least 20-times greater, and most preferably at least 100-times greater than the affinity to any other antigen. In a preferred embodiment the antibody will have an affinity that is greater than about $10^9$ liters/mol (see, e.g., Munsen, et al. (1980) *Analyt. Biochem.* 107:220-239).

II. GENERAL

The present invention provides methods for the modulation or treatment of a number of immune conditions and disorders. In particular, the present invention provides agonists and antagonists of IL-33 for the treatment and diagnosis of, e.g., asthma, allergies, arthritis, and response to intracellular pathogens, such as parasites, and response to disorders involving granulomas, e.g., tuberculosis, sarcoidosis, and Crohn's disease.

Naïve T cells appear not to express T1/ST2 on their surface, whereas expression is induced after contact with antigens on differentiated TH2 effector cells. T1/ST2 has been used as a marker for TH2-type T cells. T1/ST2 is also expressed on mast cells and fibroblasts Studies with T1/ST2 knockout mice seems to suggest that T1/ST2 does not play a part in the differentiation of naïve CD4⁺ T cells to TH2-type T cells, though these results appear to be a function of the nature of the assays used, e.g., which pathogenic organism is used in challenge studies, or which phase of TH2-response is studied. Evidence also suggests a role for T1/ST2 in early events in TH2-response (see, e.g., Kropf, et al. (2002) Infect. Immunity 70:5512-5520; Hoshino, et al. (1999) J. Exp. Med. 190:1541-1547; Senn, et al. (2000) Eur. J. Immunol. 30:1929-1938; Townsend, et al. (2000) J. Exp. Med. 191:1069-1075).

Anti-T1/ST2 antibodies have been used in a number of studies addressing the role of T1/ST2 in immune function, while other studies have examined T1/ST2 expression animal models for immune response. Treatment with anti-T1/ST2 antibodies resulted in decreased TH2-type immune responses. The antibody inhibited eosinophil infiltration, IL-5 production, and IgE-production. Infections by *Schistosoma* provoked an up-regulation of T1/ST2, e.g., as determined by assessing expression in lung and liver granulomas. Animal models for asthma, e.g., treatment with house dust mite extract or with ovalbumin, resulted in increased expression of T1/ST2 on $CD4^+$ T cells, indicating a role for T1/ST2 in allergic or asthmatic responses. Studies with BALB/c mice revealed that treating with anti-T1/ST2 antibody induced higher TH1-type response, enhancing the ability of $CD4^+$ T cells to respond to IL-12. Anti-T1/ST2 antibodies also reduce lesions due to *Leishmania major* infections, and reduced expression of TH2-type cytokines. An animal model of arthritis (collagen induced arthritis; CIA) was exacerbated by anti-T1/ST2 antibodies. In particular, T1/ST2 functions in early events in the generation of TH2-type responses. Chronic exposure to various allergens resulted in increased expression of T1/ST2 on $CD4^+$ T cells. T1/ST2 plays a role in mediating innate response, as anti-T1/ST2 antibodies exacerbate the toxic effects of lipopolysaccharide (LPS). Antibodies to T1/ST2 also modulated immune response to viruses, e.g., respiratory syncytial virus (see, e.g., Xu, et al. (1998) J. Exp. Med. 187:787-794; Lohning, et al. (1998) Proc. Natl. Acad. Sci. USA 95:6930-6935; Coyle, et al. (1999) J. Exp. Med. 190:895-902; Lohning, et al. (1999) J. Immunol. 162:3882-3889; Johnson, et al. (2003) Am. J. Respir. Crit. Care Med. 169:378-385; Kropf, et al. (2003) Infect. Immunity 71:1961-1971; Xu, et al. (1998) J. Exp. Med. 187:787-794; Kropf, et al. (2002) Eur. J. Immunol. 32:2450-2459; Swirski, et al. (2002) J. Immunol. 169:3499-3506; Sweet, et al. (2001) J. Immunol. 166:6633-6639; Walzl, et al. (2001) J. Exp. Med. 193:785-792.

IL-1 family members typically bind to a heterodimeric members of the IL-1 receptor family. It was shown that another known IL-1R family member, SIGIRR (single Ig IL-1 receptor related protein), complexes with T1/ST2 to form the functional receptor complex for IL-33. SIGIRR was originally found as an orphan IL-1R member (see, e.g., Garlanda, et al. (2004) *Proc. Natl. Acad. Sci.* 101:3522-3526; Clark, et al. (2003) *Genome Res.* 13:2265-2270; Thomassen et al. (1999) *Cytokine* 11:389-399; GenBank Accession No. NP_068577; GenBank Accession No. NM_021805; GenBank Accession No. NP_075546; and GenBank Accession No. NM_0230459). SIGIRR is a widely expressed IL-1R member.

In precipitation experiments using biotinylated mature human IL-33 (residues 112-270 of SEQ ID NO: 2), T1/ST2-Fc fusion, and SIGIRR-Fc fusion, it was shown that IL-33 could bind both receptor fusion proteins, however, the binding of IL-33 to SIGIRR was weaker as compared to IL-33 and T1/ST2 binding. To test the signaling capabilities of either or both receptors, an NF-κB-dependent assay was run. Co-expression of both T1/ST2 and SIGIRR was both necessary and sufficient to activate NF-κB signaling and MAP kinase upon stimulation with IL-33. Activation of JNK kinases was also observed.

III. AGONISTS, ANTAGONISTS, AND BINDING COMPOSITIONS

The present invention provides agonists and antagonists of IL-33, including binding compositions that specifically bind to IL-33 or to IL-33 receptor complex (T1/ST2 and SIGIRR). Binding compositions include antibodies, antibody fragments, and soluble receptors. The present invention contemplates blocking antibodies that bind to IL-33 or to IL-33R, or agonistic antibodies that stimulate signaling via the IL-33R complex. The binding compositions of the present invention also include nucleic acids that specifically hybridize to nucleic acids encoding IL-33 or IL-33R, e.g., anti-sense nucleic acids and small interference RNA (siRNA) Anti-idiotypic antibodies may also be used. Human IL-33 is disclosed by GenBank NM_033439. Regions of increased antigenicity, suitable for preparing anti-IL-33 antibodies, occur at, e.g., amino acids 1-23; 30-38; 61-78; 84-93; 99-106; 127-133; 139-144; 148-158; 166-180; 196-204; 231-237; and 252-257, of GenBank NM_033439, according to a Parker plot using Vector NTI® Suite (Informax, Inc, Bethesda, Md.).

Receptors based on these extracellular regions are not limited by these exact N-terminal and C-terminal amino acids, but may be longer or shorter, e.g., by one, two, three, or more amino acids, as long as the ligand binding properties are substantially maintained. Fusion proteins based on the soluble receptors are also contemplated, e.g., for facilitating purification or stability or for providing a functional domain, e.g., a toxic polypeptide.

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang, et al. (1999) *J. Biol. Chem.* 274:27371-27378; Baca, et al. (1997) *J. Biol. Chem.* 272:10678-10684; Chothia, et al. (1989) *Nature* 342:877-883; Foote and Winter (1992) *J. Mol. Biol.* 224:487-499; U.S. Pat. No. 6,329,511 issued to Vasquez, et al.). Muteins and variants of antibodies and soluble receptors are contemplated, e.g., pegylation or mutagenesis to remove or replace deamidating Asn residues.

Purification of antigen is not necessary for the generation of antibodies. Immunization can be performed by DNA vector immunization, see, e.g., Wang, et al. (1997) *Virology* 228:278-284. Alternatively, animals can be immunized with cells bearing the antigen of interest. Splenocytes can then be isolated from the immunized animals, and the splenocytes can fused with a myeloma cell line to produce a hybridoma (Meyaard, et al. (1997) *Immunity* 7:283-290; Wright, et al. (2000) *Immunity* 13:233-242; Preston, et al. (1997) *Eur. J. Immunol.* 27:1911-1918). Resultant hybridomas can be screened for production of the desired antibody by functional assays or biological assays, that is, assays not dependent on possession of the purified antigen. Immunization with cells may prove superior for antibody generation than immunization with purified antigen (Kaithamana, et al. (1999) *J. Immunol.* 163:5157-5164).

Antibodies will usually bind with at least a $K_D$ of about $10^{-3}$ M, more usually at least $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M (see, e.g., Presta, et al. (2001) *Thromb. Haemost.* 85:379-389; Yang, et al. (2001) *Crit. Rev. Oncol. Hematol.* 38:17-23; Carnahan, et al. (2003) *Clin. Cancer Res.* (Suppl.) 9:3982s-3990s).

Soluble receptors comprising the extracellular domains of the IL-33 receptor complex (T1/ST2 and SIGIRR) can be prepared, as the cytoplasmic, transmembrane, and extracellular regions of each of the subunits have been identified (see, e.g., Lecart, et al. (2002) Eur. J. Immunol. 32:2979-2987; Mitcham, et al. (1996) *J. Biol. Chem.* 271:5777-5783; and the Sequence Listing below).

Soluble receptors can be prepared and used according to standard methods (see, e.g., Jones, et al. (2002) *Biochim. Biophys. Acta* 1592:251-263; Prudhomme, et al. (2001) *Expert Opinion Biol. Ther.* 1:359-373; Fernandez-Botran (1999) *Crit. Rev. Clin. Lab Sci.* 36:165-224). Also provided are compositions for siRNA interference (see, e.g., Arenz and Schepers (2003) *Naturwissenschaften* 90:345-359; Sazani and Kole (2003) *J. Clin. Invest.* 112:481-486; Pirollo, et al. (2003) *Pharmacol. Therapeutics* 99:55-77; Wang, et al. (2003) *Antisense Nucl. Acid Drug Devel.* 13:169-189).

IV. THERAPEUTIC COMPOSITIONS, METHODS

The present invention provides methods for treating and diagnosing innate response, asthma, allergies, and arthritis.

To prepare pharmaceutical or sterile compositions including an agonist or antagonist of IL-33, the reagent is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom, et al. (1999) *New Engl. J. Med.* 341:1966-1973; Slamon, et al. (2001) *New Engl. J. Med.* 344:783-792; Beniaminovitz, et al. (2000) *New Engl. J. Med.* 342:613-619; Ghosh, et al. (2003) *New Engl. J. Med.* 348:24-32; Lipsky, et al. (2000) *New Engl. J. Med.* 343:1594-1602).

Antibodies, antibody fragments, and cytokines can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A preferred dose protocol is one involving the maximal dose or dose frequency that avoids significant undesirable side effects. A total weekly dose is generally at least 0.05 μg/kg body weight, more generally at least 0.2 μg/kg, most generally at least 0.5 μg/kg, typically at least 1 μg/kg, more typically at least 10 μg/kg, most typically at least 100 μg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). The desired dose of a small molecule therapeutic, e.g., a peptide mimetic, natural product, or organic chemical, is about the same as for an antibody or polypeptide, on a moles/kg body weight basis. The desired plasma concentration of a small molecule therapeutic is about the same as for an antibody, on a moles/kg body weight basis.

An effective amount for a particular patient may vary depending on factors such as the condition being treated, the overall health of the patient, the method route and dose of administration and the severity of side affects (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

Typical veterinary, experimental, or research subjects include monkeys, dogs, cats, rats, mice, rabbits, guinea pigs, horses, and humans.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing a humoral response to the reagent.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) *Goodman and Gilman's The Pharmacological Basis of Therapeutics*, $10^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., Pa.; Chabner and Longo (eds.) (2001) *Cancer Chemotherapy and Biotherapy*, Lippincott, Williams & Wilkins, Phila., Pa.). An effective amount of therapeutic will decrease the symptoms typically by at least 10%; usually by at least 20%; preferably at least about 30%; more preferably at least 40%, and most preferably by at least 50%.

The route of administration is by, e.g., topical or cutaneous application, injection or infusion by intravenous, intraperitoneal, intracerebral, intramuscular, intraocular, intraarterial, intracerebrospinal, intralesional, or pulmonary routes, or by sustained release systems or an implant (see, e.g., Sidman et al. (1983) *Biopolymers* 22:547-556; Langer, et al. (1981) *J. Biomed. Mater. Res.* 15:167-277; Langer (1982) *Chem. Tech.* 12:98-105; Epstein, et al. (1985) *Proc. Natl. Acad. Sci. USA* 82:3688-3692; Hwang, et al. (1980) *Proc. Natl. Acad. Sci. USA* 77:4030-4034; U.S. Pat. Nos. 6,350,466 and 6,316,024).

V. KITS AND DIAGNOSTIC REAGENTS

Diagnostic methods for inflammatory disorders, e.g., psoriasis, Crohn's disease, rheumatoid arthritis, asthma or allergy, atherosclerosis, and cancers, based on antibodies, nucleic acid hybridization, and the PCR method, are available.

This invention provides polypeptides of IL-33, fragments thereof, nucleic acids of IL-33, and fragments thereof, in a diagnostic kit, e.g., for the diagnosis of viral disorders, including of influenza A, and viral disorders of the respiratory tract and of mucosal tissues. Also provided are binding compositions, including antibodies or antibody fragments, for the detection of IL-33, and metabolites and breakdown products thereof. Typically, the kit will have a compartment containing either a IL-33 polypeptide, or an antigenic fragment thereof, a binding composition thereto, or a nucleic acid, such as a nucleic acid probe, primer, or molecular beacon (see, e.g., Rajendran, et al. (2003) *Nucleic Acids Res.* 31:5700-5713; Cockerill (2003) *Arch. Pathol. Lab. Med.* 127:1112-1120; Zammatteo, et al. (2002) *Biotech. Annu. Rev.* 8:85-101; Klein (2002) *Trends Mol. Med.* 8:257-260).

A method of diagnosis can comprise contacting a sample from a subject, e.g., a test subject, with a binding composition that specifically binds to a polypeptide or nucleic acid of IL-33 or IL-33 receptor. The method can further comprise contacting a sample from a control subject, normal subject, or normal tissue or fluid from the test subject, with the binding composition. Moreover, the method can additionally comprise comparing the specific binding of the composition to the test subject with the specific binding of the composition to the normal subject, control subject, or normal tissue or fluid from the test subject. Expression or activity of a test sample or test subject can be compared with that from a control sample or control subject. A control sample can comprise, e.g., a sample of non-affected or non-inflamed tissue in a patient suffering from an immune disorder. Expression or activity from a control subject or control sample can be provided as a predetermined value, e.g., acquired from a statistically appropriate group of control subjects.

The kit may comprise, e.g., a reagent and a compartment, a reagent and instructions for use, or a reagent with a compartment and instructions for use. The reagent may comprise an agonist or antagonist of IL-33, or an antigenic fragment thereof, a binding composition, or a nucleic acid in a sense and/or anti-sense orientation. A kit for determining the binding of a test compound, e.g., acquired from a biological sample or from a chemical library, can comprise a control compound, a labeled compound, and a method for separating free labeled compound from bound labeled compound. The control compound can comprise a segment of the polypeptide of IL-33 or IL-33 receptor or a nucleic acid encoding IL-33 or IL-33 receptor. The segment can comprise zero, one, two, or more antigenic fragments.

A composition that is "labeled" is detectable, either directly or indirectly, by spectroscopic, photochemical, biochemical, immunochemical, isotopic, or chemical methods. For example, useful labels include $^{32}P$, $^{33}P$, $^{35}S$, $^{14}C$, $^{3}H$, $^{125}I$, stable isotopes, fluorescent dyes, electron-dense reagents, substrates, epitope tags, or enzymes, e.g., as used in enzyme-linked immunoassays, or fluorettes (Rozinov and Nolan (1998) *Chem. Biol.* 5:713-728).

Diagnostic assays can be used with biological matrices such as live cells, cell extracts, cell lysates, fixed cells, cell cultures, bodily fluids, or forensic samples. Conjugated antibodies useful for diagnostic or kit purposes, include antibodies coupled to dyes, isotopes, enzymes, and metals, see, e.g., Le Doussal, et al. (1991) *New Engl. J. Med.* 146:169-175; Gibellini, et al. (1998) *J. Immunol.* 160:3891-3898; Hsing and Bishop (1999) *New Engl. J. Med.* 162:2804-2811; Everts, et al. (2002) *New Engl. J. Med.* 168:883-889. Various assay formats exist, such as radioimmunoassays (RIA), ELISA, and lab on a chip (U.S. Pat. Nos. 6,176,962 and 6,517,234).

Gene expression data is useful tool in the diagnosis and treatment of diseases and pathological conditions (see, e.g., Li and Wong (2001) *Genome Informatics* 12:3-13; Lockhart, et al. (1996) *Nature Biotechnol.* 14:1675-1680; Homey, et al. (2000) *J. Immunol.* 164:3465-3470; Debets, et al. (2000) *J. Immunol.* 165:4950-4956).

VI. USES

The present invention provides methods for the treatment and diagnosis of inflammatory and immune disorders, including inappropriate or ineffective response to infection. Provided are methods relating to, e.g., asthma, allergies, arthritis, disorders involving eosinophilic inflammation, and disorders involving pathogenic or ineffective TH2-type response.

The present invention provides methods for stimulating immune defense against bacteria, parasites, and viruses, intracellular pathogens, and cancers and tumors. Provided are methods for the treatment of intracellular bacteria. Intracellular bacterial species include *Salmonella* sp., *Shigella* sp., *Listeria* sp., *Francisella* sp., *Mycobacteria* sp. (tuberculosis; leprosy), *Legionella* sp., *Rickettsia* sp., *Orienta* sp., *Ehrlichia* sp., *Anaplasma* sp., *Neorickettsia* sp., *Chlamydia* sp., and *Coxiella* sp. Additionally, IFNgamma mediates response to parasites, e.g., *Plasmodia* sp. (malaria), *Toxoplasma* sp., *Leishmania* sp., *Trypanosoma* sp., and *Cryptosporidium* sp. Provided are methods for treating viruses, e.g., HIV, orthopoxviruses, such as variola virus and vaccinia virus (smallpox), and herpesviruses, including alphaherpesviruses, e.g., Herpes Simplex virus, and betaherpesviruses, e.g., Cytomegalovirus. Also provided are methods for the treatment of chronic inflammatory disorders (see, e.g., Kent, et al. (2000) *Vaccine* 18:2250-2256; Ismail, et al. (2002) *FEMS Microbiol. Lett.* 207:111-120; Kaufmann (2001) *Nature Revs. Immunol.* 1:20-30; Goebel and Gross (2001) *TRENDS Microbiol.* 9:267-273; Heussler, et al. (2001) *Int. J. Parasitol.* 31:1166-1176; Luder, et al. (2001) Carsten, et al. (2001) *TRENDS Parasitol.* 17:480-486; Rook, et al. (2001) *Eur. Resp. J.* 17:537-557; Stenger and Rollinghoff (2001) *Ann. Rheum. Dis.* 60:iii43-iii46; Haas, et al. (2002) *Am. J. Dermatopathol.* 24:319-323; Dorman and Holland (2000) *Cytokine Growth Factor Revs.* 11:321-333; Smith, et al. (2002) *J. Gen. Virol.* 83 (Pt. 12) 2915-2931; Cohrs and Gilden (2001) *Brain Pathol.* 11:465-474; Tannenbaum and Hamilton (2002) *Sem. Cancer Biol.* 10:113-123; Ikeda, et al. (2002) *Cytokine Growth Factor Revs.* 13:95-109; Klimp, et al. (2002) *Crit. Rev. Oncol. Hematol.* 44:143-161; Frucht, et al. (2001) *TRENDS Immunol.* 22:556-560).

The present invention provides methods of treating or diagnosing a proliferative condition or disorder, e.g., cancer of the uterus, cervix, breast, prostate, testes, penis, gastrointestinal tract, e.g., esophagus, oropharynx, stomach, small or large intestines, colon, or rectum, kidney, renal cell, bladder, bone, bone marrow, skin, head or neck, skin, liver, gall bladder, heart, lung, pancreas, salivary gland, adrenal gland, thyroid, brain, ganglia, central nervous system (CNS) and peripheral nervous system (PNS), and immune system, e.g., spleen or thymus. The present invention provides methods of treating, e.g., immunogenic tumors, non-immunogenetic tumors, dormant tumors, virus-induced cancers, e.g., epithelial cell cancers, endothelial cell cancers, squamous cell carcinomas, papillomavirus, adenocarcinomas, lymphomas, carcinomas, melanomas, leukemias, myelomas, sarcomas, teratocarcinomas, chemically-induced cancers, metastasis, and angiogenesis. The invention also contemplates reducing tolerance to a tumor cell or cancer cell antigen, e.g., by modulating activity of a regulatory T cell (Treg) (see, e.g., Ramirez-Montagut, et al. (2003) *Oncogene* 22:3180-3187; Sawaya, et al. (2003) *New Engl. J. Med.* 349:1501-1509; Farrar, et al. (1999) *J. Immunol.* 162:2842-2849; Le, et al. (2001) *J. Immunol.* 167:6765-6772; Cannistra and Niloff (1996) *New Engl. J. Med.* 334:1030-1038; Osborne (1998) *New Engl. J. Med.* 339:1609-1618; Lynch and Chapelle (2003) *New Engl. J. Med.* 348:919-932; Enzinger and Mayer (2003) *New Engl. J. Med.* 349:2241-2252; Forastiere, et al. (2001) *New Engl. J. Med.* 345:1890-1900; Izbicki, et al. (1997) *New Engl. J. Med.* 337:1188-1194; Holland, et al. (eds.) (1996) *Cancer Medicine Encyclopedia of Cancer, 4$^{th}$ ed.*, Academic Press, San Diego, Calif.).

The present invention provides methods for treating a proliferative condition, cancer, tumor, or precancerous condition such as a dysplasia, with an agonist or antagonist of IL-33, with at least one additional therapeutic or diagnostic agent. The at least one additional therapeutic or diagnostic agent can be, e.g., a cytokine or cytokine antagonist, such as interferon-alpha, or anti-epidermal growth factor receptor, doxorubicin, epirubicin, an anti-folate, e.g., methotrexate or fluoruracil, irinotecan, cyclophosphamide, radiotherapy, hormone or anti-hormone therapy, e.g., androgen, estrogen, anti-estrogen, flutamide, or diethylstilbestrol, surgery, tamoxifen, ifosfamide, mitolactol, an alkylating agent, e.g., melphalan or cis-platin, etoposide, vinorelbine, vinblastine, vindesine, a glucocorticoid, a histamine receptor antagonist, an angiogenesis inhibitor, radiation, a radiation sensitizer, anthracycline, vinca alkaloid, taxane, e.g., paclitaxel and docetaxel, a cell cycle inhibitor, e.g., a cyclin-dependent kinase inhibitor, a monoclonal antibody, a complex of monoclonal antibody and toxin, a T cell adjuvant, bone marrow transplant, or antigen presenting cells, e.g., dendritic cell therapy. Vaccines can be provided, e.g., as a soluble protein or as a nucleic acid encoding the protein (see, e.g., Le, et al., supra; Greco and Zellefsky (eds.) (2000) *Radiotherapy of Prostate Cancer*, Harwood Academic, Amsterdam; Shapiro and Recht (2001) *New Engl. J. Med.* 344:1997-2008; Hortobagyi (1998) *New Engl. J. Med.* 339:974-984; Catalona (1994) *New Engl. J. Med.* 331:996-1004; Naylor and Hadden (2003) *Int. Immunopharmacol.* 3:1205-1215; The Int. Adjuvant Lung Cancer Trial Collaborative Group (2004) *New Engl. J. Med.* 350:351-360; Slamon, et al. (2001) *New Engl. J. Med.* 344:783-792; Kudelka, et al. (1998) *New Engl. J. Med.* 338:991-992; van Netten, et al. (1996) *New Engl. J. Med.* 334:920-921).

A number of biomarkers and methods for scoring inflammatory disorders, e.g., psoriasis, Crohn's disease, and rheumatoid arthritis are available (see, e.g., Bresnihan (2003) *Arthritis Res. Ther.* 5:271-278; Barnero and Delmas (2003) *Curr. Opin. Rheumatol.* 15:641-646; Gionchetti, et al. (2003) *Dig. Dis.* 21:157-167; Wiik (2002) *Autoimmune Rev.* 1:67-72; Sostegni, et al. (2003) *Aliment Pharmacol. Ther.* 17 (Suppl.2):11-17).

Biomarkers and methods for scoring cancer are also described (see, e.g., Alison (ed.) (2001) *The Cancer Handbook*, Grove's Dictionaries, Inc., St. Louis, Mo.; Oldham (ed.) (1998) *Principles of Cancer Biotherapy,* 3$^{rd}$. ed., Kluwer Academic Publ., Hingham, Mass.; Thompson, et al. (eds.) (2001) *Textbook of Melanoma*, Martin Dunitz, Ltd., London, UK; Devita, et al. (eds.) (2001) *Cancer*: Principles *and Practice of Oncology, 6$^{th}$ ed.*, Lippincott, Phila, Pa.; Holland, et al. (eds.) (2000) *Holland-Frei Cancer Medicine*, BC Decker, Phila., Pa.; Garrett and Sell (eds.) (1995) *Cellular Cancer Markers*, Humana Press, Totowa, N.J.; MacKie (1996) *Skin Cancer, 2$^{nd}$ ed.*, Mosby, St. Louis; Moertel (1994) *New Engl. J. Med.* 330:1136-1142; Engleman (2003) *Semin. Oncol.* 30(3 Suppl. 8):23-29; Mohr, et al. (2003) *Onkologie* 26:227-233).

The broad scope of this invention is best understood with reference to the following examples, which are not intended to limit the inventions to the specific embodiments.

EXAMPLES

I. General Methods

Standard methods in biochemistry and molecular biology are described (see, e.g., Maniatis, et al. (1982) *Molecular Cloning, A Laboratory Manual*, Cold Spring Harbor Laboratory Press, Cold Spring Harbor, N.Y.; Sambrook and Russell (2001) *Molecular Cloning, 3$^{rd}$ ed.*, Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology, Vols.* 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory, Piscataway, N.J., pp.* 384-391). Methods for the production, purification, and fragmentation of polyclonal and monoclonal antibodies are described (Coligan, et al. (2001) *Current Protocols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol.* 4, John Wiley, Inc., New York).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry, $2^{nd}$ ed.*; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (see, e.g., Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Methods for using animal models, e.g., knockout mice, and cell-based assays for the testing, evaluation, and screening of diagnostic, therapeutic, and pharmaceutical agents are available (see, e.g., Car and Eng (2001) *Vet. Pathol.* 38:20-30; Kenyon, et al. (2003) *Toxicol. Appl. Pharmacol.* 186:90-100; Deurloo, et al. (2001) *Am. J. Respir. Cell Mol. Biol.* 25:751-760; Zuberi, et al. (2000) *J. Immunol.* 164:2667-2673; Temelkovski, et al. (1998) *Thorax* 53:849-856; Horrocks, et al. (2003) *Curr. Opin. Drug Discov. Devel.* 6:570-575; Johnston, et al. (2002) *Drug Discov. Today* 7:353-363).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

II. Interleukin-100

Similarity of the amino acid sequence of human IL-33 to other members of the IL-1 family is as follows. Similarity with IL-1Ra is 34% similarity; IL-1delta is 36%; IL-1F10 is 36%; IL-1zeta is 9%; IL-1F8 is 32%; IL-1epsilon is 40%; and IL-1F9 is 31%.

Interleukin-100 was discovered by using computational sequence analyses and identified as a new IL-1 family member by secondary structure comparison with members of the IL-1 family, respectively IL-1beta and IL-18. IL-1 family members are highly inflammatory regulators of the immune system, released in response to pathogenic challenges. Human and mouse homologs of IL-33 were identified as well as a rat and dog IL-33. Gene expression analysis showed that human IL-33 was expressed in epithelial cells, smooth muscle cells, and mesangial cells. Upon stimulation with IL-1β and TNF-α, human IL-33 mRNA levels are highly induced in primary normal human dermal and lung fibroblasts as well as in bronchial smooth muscle cells. Expression of IL-33 mRNA in psoriatic skin samples as well as in lung pulmonary alveolar proteinosis was significantly elevated.

Similar to IL-1 and IL-18, IL-33 has no signal peptide. In stead, IL-33 is made and secreted as a large preproprotein that requires extensive processing to release the mature, biologically active form. It is likely that prepro IL-33 is processed by a caspase. We identified a caspase cleavage site in the protein sequence and showed that in vitro translated human IL-33 is cleaved by recombinant constitutively active caspase-1. To investigate the putative biological role of IL-33, recombinant proteins were expressed and purified in *E. coli*. Therefore, the IL-33 gene was cloned into a pET3a bacterial expression vector. The N-terminus of the recombinant protein was selected by comparing the mature sequence of IL-33 to IL-1β and IL-18 so that the mature, biologically active protein would lack the pro-domain. Amino acid 112 of the full-length protein was selected as the N-terminal amino acid. Recombinant protein was expressed and purified from *E. coli*. In vivo studies were carried out. The intraperitoneal (IP) injection of recombinant human IL-33 into mice (C57BL/6J), with a dosage of either 5 ug/day or 50 ug/day, led to severe eosinophilia and splenomegaly after 7 days. Serum levels of several cytokines were tested on day 3 and day 7. An induction of IL-5 up to 10000 pg/ml in the 50 ug rhIL-33/day group and up to 1000 pg/ml in the 5 ug rhIL-33/day group was observed on day 3. The serum levels of IL-5 decreased to 1100 pg/ml in the 50 ug rhIL-33/day group and in the 5 ug rhIL-33/day group to 500 pg/ml. IL-13 serum levels were also detectable at day 7 after treatment with either 5 ug or 50 ug IL-33/day at 30 pg/ml and 100 pg/ml, respectively. No IL-5 and IL-13 could be detected in the PBS-treated control group. Furthermore, no elevated levels for IFN-γ, TNF-α, IL-12, IL-10, IL-6, IL-4, IL-2 or MCP-1 could be detected in IL-33 treated mice or in the control group.

After IP injection of 50 ug rhIL-33/day for 2 days liver lymphocytes were harvested. Cells were plated into culture dishes with 2×10e6/ml of culture medium and were stimulated with 50 ng/ml PMA and 1 uM ionomycin for 4 hr. During the last 2 hr, Brefelding A, a secretion inhibitor, was added. Cells were surface stained for CD3 and NK1.1 and intracellularly stained either for IL-5 or IL-4 and analyzed by FACS. CD3/NK1.1 positive liver lymphocytes cells derived from mice treated for 2 days with IL-33 showed an accumulation of IL-5 and IL-4. These results suggest that IL-33 activates NKT cells to secrete IL-4 and IL-5.

To test if IL-33 binds NKT cells, biotinylated IL-33 was used for a binding experiment. Human NKT cells, derived from PBMCs, were incubated either with Strepdavidin-PE or biotinylated rhIL-33 and Strepdavidin-PE. The stained cells were analyzed by FACS. Binding of rhIL-33 to human NKT cells was observed. This binding could be competed with unbiotinylated rhIL-33.

IL-1 family members exert their biological response by interacting with cell surface receptors. We have identified the orphan IL-1 receptor ST2/T1 as a cellular receptor for IL-33. FACS staining of a mouse mast cell line with a ST2/T1-specific monoclonal antibody showed that this mast cell line expresses the ST2/T1 receptor. This staining could be specifically and dose-dependently competed by incubating the mast cell line with IL-33 protein.

NKT cells are essential for airway inflammation and the production of IL-4 and IL-13 in allergen-induced airway-hyper-reactivity in mouse models of asthma. The induction of IL-5 and IL-13 by IL-33 in NKT cells suggests that IL-33 can play a role in the induction of these diseases. The generation of therapeutic antibodies neutralizing IL-33 may be beneficial in the treatment of these diseases.

NKT cells have been implicated in many diseases. Identification of IL-33 as a modulator of NKT cells suggest that IL-33 can affect other diseases, such as lupus, multiple sclerosis, malignancies, airway inflammation and infectious diseases. The induction of Th2 cytokines by IL-33, such as IL-5 and IL-13, may help in the protection against microbial infection or in the protection against tumors.

IL-1 family members typically bind to two different members of the IL-1 receptor family to form a complete receptor complex. The identification of IL-33 and ST2/T1 as one of the subunits that make up the receptor for IL-33, makes it possible to identify the second IL-33 receptor subunit. Identification of the complete IL-33 receptor will allow detailed identification of the biological responses induced by IL-33.

Real time PCR analysis using Taqman revealed that IL-33 was expressed by a number of cells and tissues (Table 1). The present invention provides agonists and antagonists of IL-33 for the modulation of inflammatory and autoimmune disorders and conditions, e.g., psoriasis, asthma, allergies, and inflammatory bowel disease, e.g., gastric inflammation, ulcerative colitis, Crohn's disease, celiac disease, and irritable bowel syndrome.

TABLE 1

Real time PCR analysis of IL-33 expression, relative to ubiquitin (1.0).

| Human skin psoriasis vulgaris | | Human skin, normal adjacent | |
|---|---|---|---|
| Skin sample no. | Expression | Skin sample no. | Expression |
| PS-034 | 757 | PS-034 | 261 |
| PS-037 | 731 | PS-037 | 267 |
| PS-028 | 443 | PS-028 | 285 |
| PS-025 | 446 | PS-025 | 261 |
| PS-023 | 602 | PS-023 | 235 |
| Colon control | | 0.5 | |
| Colon Crohn's no. 4003197A | | 87 | |
| Colon Crohn's no. 9609C144 | | 125 | |
| Colon Crohn's no. 403242A | | 114 | |

Expression of cytokines with *Nippostrongylus brasiliensis* infection, as determined by real time PCR Taqman analysis.

| sample | IL-25 | IL-13 | IL-4 | IL-5 | IL-33 |
|---|---|---|---|---|---|
| | Cytokine tested | | | | |
| Untreated stomach | 0.86 | 0.03 | 0.51 | 0.01 | 9.43 |
| stomach 2 day | 1.46 | 0.69 | 0.09 | 0.02 | 56.4 |
| stomach 4 day | 0.73 | 0.67 | 0.39 | 0.09 | 80.32 |
| stomach 8 day | 1.04 | 3.30 | 0.33 | 0.44 | 84.9 |
| stomach 11 days | 0.27 | 1.22 | 1.77 | 0.01 | 8.86 |
| stomach 16 days | 0.35 | 0.38 | 1.31 | 0.12 | 3.43 |
| Untreated control lung | 0.29 | 0.01 | 0.57 | 0.66 | 56.8 |
| Lung nippo 2 days | 0.91 | 0.37 | 0.61 | 0.65 | 90.37 |
| Lung nippo 4 days | 0.59 | 13.34 | 4.65 | 3.78 | 356.49 |
| Lung nippo 8 days | 0.36 | 55.88 | 8.78 | 1.14 | 48.76 |
| Lung nippo 11 days | 0.35 | 33.93 | 16.05 | 2.11 | 116.79 |
| Lung nippo 16 days | 0.04 | 23.77 | 25.48 | 0.84 | 30.65 |

IL-33 induction by IL-1β plus TNF-α (8 hours) was compared with IL-33 induction with medium alone. Induction was studied in the indicated cell type (Table 2).

TABLE 2

IL-33 induction. ND means not detectable. Numbers are relative to ubiquitin (1.0).

| Cell | IL-1β plus TNF-α | Medium only |
|---|---|---|
| NHDF | 3250 | 50 |
| NHEK | ND | ND |
| NHBE | 25 | 25 |
| PAEC | 100 | 200 |
| NHLF | 25 | ND |
| BSMC | 2025 | 350 |

In vitro translated human IL-33 was found to be cleaved by caspase-1. Without caspase treatment, analysis by SDS PAGE revealed a band at about 32 kDa, corresponding to pro-human IL-33. Treatment with caspase-1 for 1 hour at 37° resulted in two bands of about equal intensity, one corresponding to pro-IL-33, and the other migrating at about 20-22 kDa (mature human IL-33). Treatment for 2 hours at 37° resulted in the same two bands, but with about two thirds of the protein migrating at about 22 kDa. Similar studies demonstrated that in vitro translated human IL-33 could also be cleaved by elastase or by cathepsin G, to species migrating at about 20-22 kDa, whereas MMP-3 treatment did not result in cleavage under the conditions used. Amino acid 112 of IL-33 is believed to be the position of cleavage, producing the mature IL-33, due to homology with other IL-1 family members.

T1/ST2 was identified as at least one subunit of the receptor for human IL-33. Expression of T1/ST2 was as follows (Table 3).

TABLE 3

| Expression of T1/ST2 by human or mouse cells. | | |
|---|---|---|
| Cell type | Human cells | Mouse cells |
| TH1-type T cells | −/+ | −/+ |
| TH2-type T cells | −/+ | +++ |
| Mast cells | +++ | ++ |
| monocytes/PBMC treated with LPS | ++ | not determined |
| Dendritic cells ex BM | (not determined) | + |

Human IL-33 was cloned in a pET3a vector, and expressed in *E. coli*. The cloned protein began with amino acid 112, and was 158 amino acids long (18 kDa). IPTG was used to induced expression, and the protein was found to be water-soluble. The expressed protein was purified using a A-column and Sephadex gel filtration. The purified preparation was tested for endotoxin, where the results demonstrated about 0.023 EU per microgram protein. Analysis by SDS PAGE using a non-reducing conditions revealed that at least 95% of the protein migrated at a single molecular weight of 18 kDa.

IL-33 was injected intraperitoneally (i.p.) into B6/Balb/c mice. Three groups of mice were used: (1) Injection with phosphate buffered saline (PBS); (2) hIL-33 (5 micrograms/day); and (3) hIL-33 (50 micrograms/day). The protocol also involved injections (i.p.) for 3 days, with sacrifice after three days of treatment, or injections (i.p.) for 7 days, with sacrifice after seven days of treatment. Blood, serum, blood smears, white blood cell differentials, histology, was performed. Thymus/spleen cells suspensions were analyzed by FACS analysis.

IL-33 treatment induces IL-5 and IL-13, as determined by measuring serum levels of IL-5 and IL-13 (Table 4). The cytokines IL-4, IL-5, and IL-13 were also measured in various organs with IL-33 administration. The organs tested were thymus, lung, spleen, and liver. These three cytokines were all found to be induced, as determined after 7 days treatment with IL-33. Increases were found at both levels of IL-33 (5 and 50 microgram IL-33). For example, in lung, IL-4, IL-5, and IL-13 expression with saline treatment was about 1.0, or less. But with IL-33 (50 micrograms), expression of IL-4 was 8.0; of IL-5 was 11.0; and of IL-13 was 41.0. IL-33 treatment also provoked increases in serum IgE and IgA. With 7 days treatment, IgE levels were 30,000 ng/ml (PBS) and 17,000 ng/ml (50 micrograms IL-33). With 7 days treatment, IgA levels were 90 ng/ml (PBS) and 420 ng/ml (50 micrograms IL-33). IL-33 treatment also resulted in splenomegaly, where spleen mass in the PBS (control) treated mouse was about 80 mg, 5 micrograms with IL-33 for 7 days (150 mg spleen), and 50 micrograms with IL-33 for 7 days (190 mg spleen). IL-33 treatment also produced extramedullary hematopoiesis in the spleen, and thymus hypoplasia (decrease in thymus size), and hypoplasia of the cortex of the thymus.

TABLE 4

| IL-33 treatment and white blood cell counts, platelet counts, and cytokine levels, at days 3 and 7. | | | |
|---|---|---|---|
| | PBS | 5 micrograms IL-33/.day | 50 micrograms IL-33/day |
| White blood cell counts (white blood cells/microliter blood) | | | |
| Day 3 | 12,000 | 12,000 | 14,000 |
| Day 7 | 12,000 | 20,000 | 25,000 |
| Platelets (platelets/microliter blood) | | | |
| Day 3 | | | |
| Day 7 | 1,300,000 | 1,000,000 | 600,000 |
| Neutrophils | | | |
| Day 3 | 500 | 350 | 520 |
| Day 7 | 750 | 700 | 1200 |
| Lymphocytes | | | |
| Day 3 | 10,000 | 10,000 | 7,500 |
| Day 7 | 11,000 | 15,500 | 18,000 |
| Monocytes | | | |
| Day 3 | 230 | 130 | 200 |
| Day 7 | 400 | 250 | 300 |
| Eosinophils | | | |
| Day 3 | 420 | 220 | 130 |
| Day 7 | 500 | 2000 | 1750 |
| Serum levels of IL-5 (pg/ml) | | | |
| Day 3 | ND | 500 | 7500 |
| Day 7 | ND | 500 | 1100 |
| Serum levels of IL-7 (pg/ml) | | | |
| Day 7 | ND | 40 | 78 |

Transformed and non-transformed cells were injected into mice, followed by an incubation period of the cells within the mouse, and retrieval and purification of the injected cells, with assessment of T1/ST2 expression (Table 5). Non-transformed mammary gland cells and ras-transformed mammary gland cells were used. With injection of the ras-transformed cells into a host immune-deficient nude mouse, the ras-transformed cells expressed T1/ST2 at increased levels, that is, expression was 103 (Table 5). With injection of the ras-transformed cells into a host mouse having an intact immune system, retrieval of the transformed cell, and Taqman® analysis, revealed greater increases in T1/ST2 expression. It is believed that these increases in T1/ST2 expression reflect increases in soluble T1/ST2, where the soluble T1/ST2 acts as a decoy. When soluble T1/ST2 acts as a decoy, it binds to IL-33, and inhibits the host from mounting a TH2-type immune response against the tumor cells. The host mice with intact immune systems that were used, were Xtb mice and XBalb mice (Table 6). The soluble version of T1/ST2 (also known as Fit 1) is described (see, e.g., Bergers, et al. (1994) *EMBO J.* 13:1176-1188; Reikerstorfer, et al. (1995) *J. Biol. Chem.* 270:17645-17648).

IL-33 was administered to mice harboring 4T1 breast cancer. Administered IL-33 was effective in reducing tumor size (Table 6). The present invention provides agonists of IL-33, e.g., IL-33 or a nucleic acid encoding IL-33, for the treatment of proliferative conditions, including cancers and tumors.

TABLE 5

Injection of ras-transformed cells into nude mice and immunocompetant mice, followed by Taqman analysis of T1/ST2 expression by recovered ras-transformed cells.

| | Expression of T1/ST2 |
|---|---|
| Nude mouse host | 103 |
| Xtb mouse host | 421 |
| XBalb mouse host | 669 |

TABLE 6

Administered IL-33 reduces tumor size in mice.

| | Tumor size ($mm^3$) | | | | | | | | | | |
|---|---|---|---|---|---|---|---|---|---|---|---|
| Treatment | 23 | 24 | 25 | 26 | 27 | 28 | 29 | 30 | 31 | 32 | 33 |
| IL-33 | 175 | 125 | 125 | 200 | 180 | 170 | 205 | 200 | 200 | 240 | 240 |
| no IL-33 | 175 | 200 | 225 | 240 | 280 | 300 | 370 | 405 | 430 | 470 | 500 |

Taqman analysis of human tissue samples revealed decreased expression of IL-33 in various cancers, e.g., breast cancer and ovarian cancer (Table 7). The results indicate that the tumor cells refrain from producing IL-33, in order to avoid activating the immune system to mount an anti-tumor response (Table 7).

TABLE 7

Real time PCR analysis of IL-33 expression by human cancer tissues.

| | Cancerous tissue | Normal adjacent tissue |
|---|---|---|
| Human breast 6221 (infiltrating duct) | 30.4 | 435.0 |
| Human breast 6612 (infiltrating duct) | 59.7 | 54.7 |
| Human breast 6652 (infiltrating duct) | 2.4 | 292.0 |
| Human breast 7748/02 lobular | 2.6 | 411.0 |
| Human breast 7156 lobular | 77.4 | 189.1 |
| Human ovary papillary serous cystadenocarcinoma 1590 | 1872.7 | 609.4 |
| Human ovary papillary serous cystadenocarcinoma 3572/02 | 206.6 | 793.9 |
| Human ovary papillary serous cystadenocarcinoma 246869 | 235.1 | 1052.7 |

IL-33 treatment prolonged experimental autoimmune encephalitis, an animal model for multiple sclerosis. EAE was induced by proteolipid protein (PLP) (Kjellen, et al. (2001) *J. Neuroimmunol.* 120:25-33; Laman, et al. (2001) *J. Neuroimmunol.* 119:124-130; Fife, et al. (2001) J. Immunol. 166:7617-7624). Three groups of mice were used for injections of PBS, 0.5 micrograms IL-33, or 2.0 micrograms of IL-33, with daily i.p. injections from day 0 to day 12. Disease scores were assessed on days 7 to 23 (Table 8). The results demonstrated that in PBS-treated mice, the disease spontaneously resolved. However, with treatment with either dose of IL-33, the disease was prolonged, higher than that found with PBS treatment, and maintained itself at a disease score of between 2.5-3.0 (Table 8). The present invention provides an antagonist of IL-33 for the treatment of autoimmune disorders, including autoimmune disorders of the central nervous system, e.g., multiple sclerosis.

TABLE 8

EAE disease score in mice at selected days after treatment with PBS or with IL-33.

| | Day 11 | Day 13 | Day 15 | Day 17 | Day 19 | Day 21 |
|---|---|---|---|---|---|---|
| PBS | 0 | 2.05 | 1.75 | 0.45 | 0.20 | 0.0 |
| 0.5 micrograms IL-33 | 0 | 0.75 | 1.15 | 2.4 | 2.9 | 2.9 |
| 2.0 micrograms IL-33 | 0 | 1.95 | 1.95 | 3.1 | 2.3 | 2.55 |

IL-33 treatment led to IL-5 induction in NKT cells. NKT cells were identified by the presence of both the NK1.1 marker and the CD3 marker. Black-6 mice were treated for two days with PBS or 50 micrograms/day of IL-33. Liver lymphocytes were isolated, and restimulated with PMA ionomycin for 3 hours and brefeldin for 1 hour. The results demonstrated that IL-33 induced IL-5 in NKT cells.

Anti-T1/ST2 antibody was tested for its ability to bind wild type mast cells (WTMC), and the influence of added IL-33 on binding of this antibody to the mast cells. Adding IL-33 abolished the ability of anti-T1/ST2 antibody to bind the mast cells, demonstrating that the receptor of IL-33 is T1/ST2.

III. In Vivo Effects of IL-33 Antibody Treatment

A mouse monoclonal antibody against human IL-33 was raised using methods well known in the art (see above). To test the ability of this antibody to antagonize IL-33 activity, Balb/c mice were injected subcutaneously with 0.2 mg of anti-IL-33 antibody on day 0. On day 1, the mice were injected intraperitonally with 100 ng of mIL-33. Serum was collected on day 2, and IL-5 levels measured. Treatment with the anti-IL-33 antibody resulted in little to no production of IL-5 when compared to mice treated with IL-33 alone and mice treated with isotype control antibody and IL-33 (See FIG. 1).

IV. Treatment of Collagen Induced Arthritis (CIA)

B10.RIII mice, known to be susceptible to developing CIA, were injected with bovine collagen type II (bovine CII; Sigma) in complete Freund's adjuvant (Difco). Mice were injected above the tail base with 100 ul of a 1 mg/ml emulsion of bovine CII. A second boost dose was administered at day 21. Mice were assessed by the following clinical scale: 0=normal; 1=redness and/or swelling at one joint/site; 2=redness and/or swelling at more than on joint/site; and 3=redness and or swelling in the entire paw. CIA induced mice have a percent disease onset of 70-90%.

Figure 2:
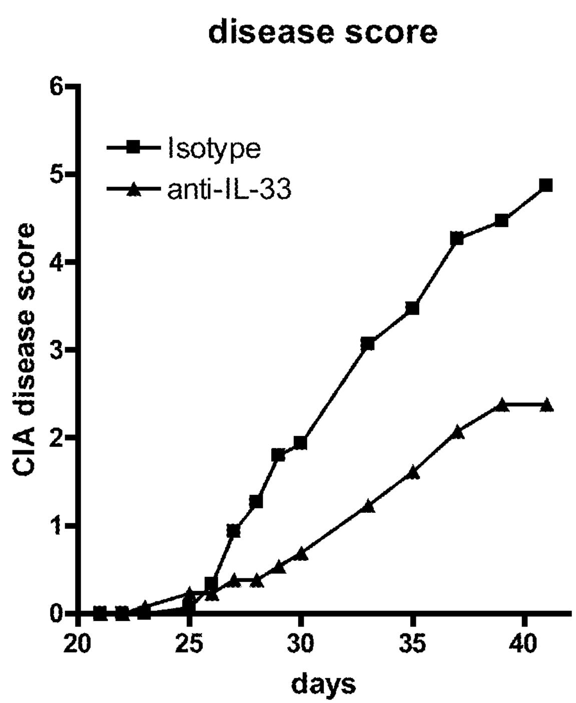
FIG. 2 shows CIA disease scores for anti-IL-33 and isotype control treated mice.
Figure 3:
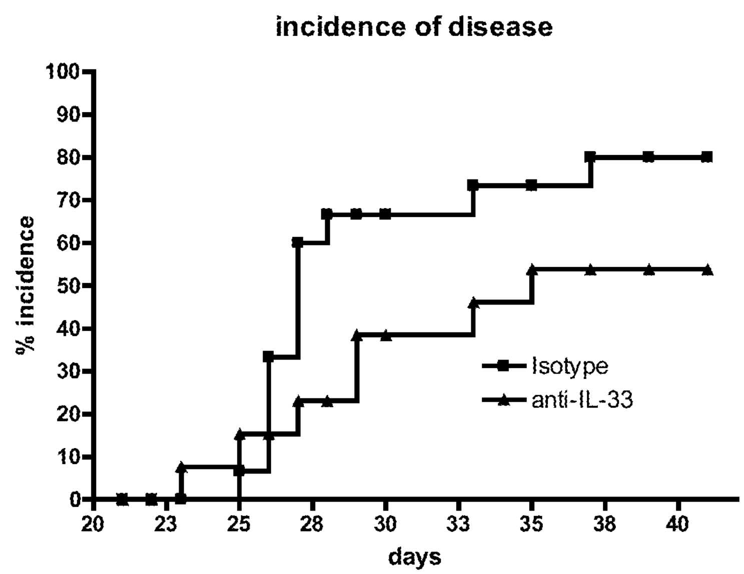
FIG. 3 shows the incidence of CIA in anti-IL-33 and isotype control treated mice.
Figure 4:
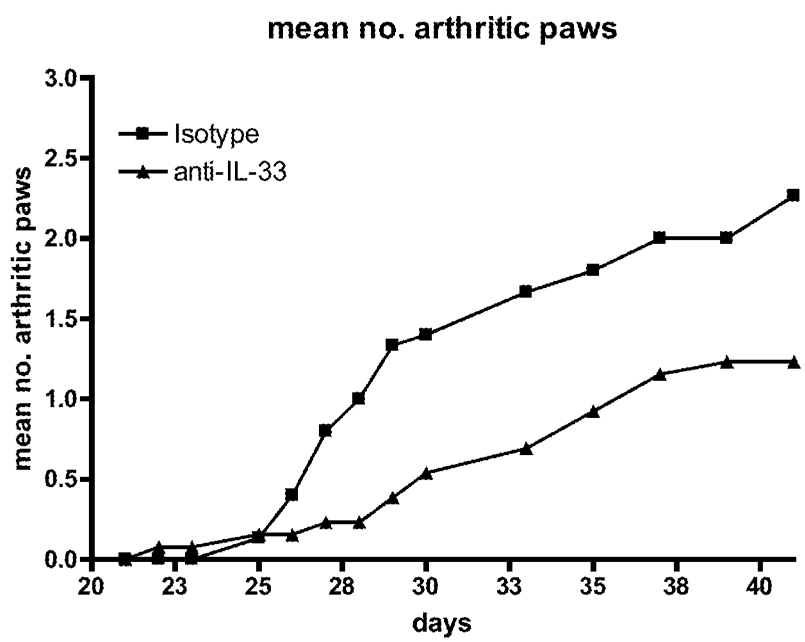
FIG. 4 shows the mean number of arthritic paws in mice treated with anti-IL-33 antibody or isotype control antibody.

Mice were treated at day 23 with 1 mg of anti-IL-33 antibody or isotype control antibody. Antibodies were administered every 7 days for two more treatments. Anti-IL-33 treated mice showed decreased disease scores as well as a lower percent incidence of disease onset (see FIGS. 2 and 3). The anti-IL-33 treated mice also had a lower mean number of arthritic paws (see FIG. 4).

V. Treatment of Experimental Autoimmune Encephilitis (EAE)

Figure 5:
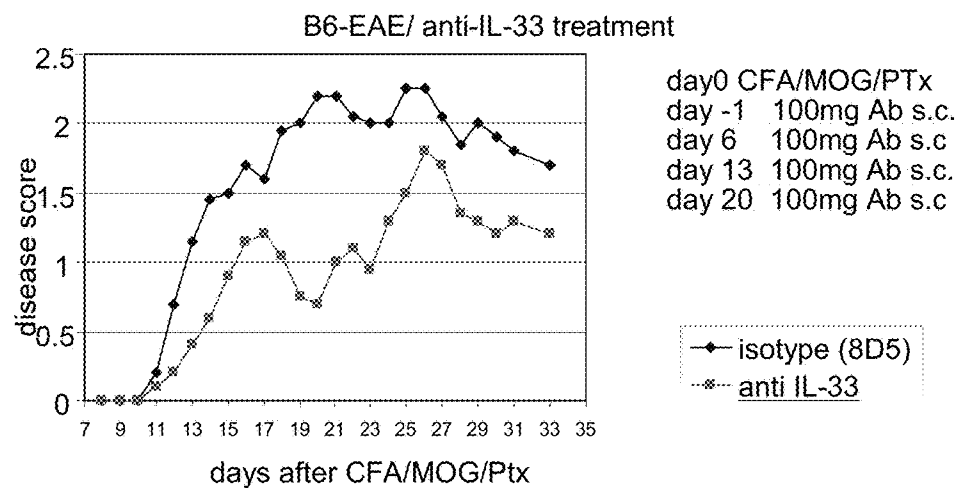
FIG. 5 shows the EAE disease scores of anti-IL-33 and isotype control treated mice.
Figure 6:
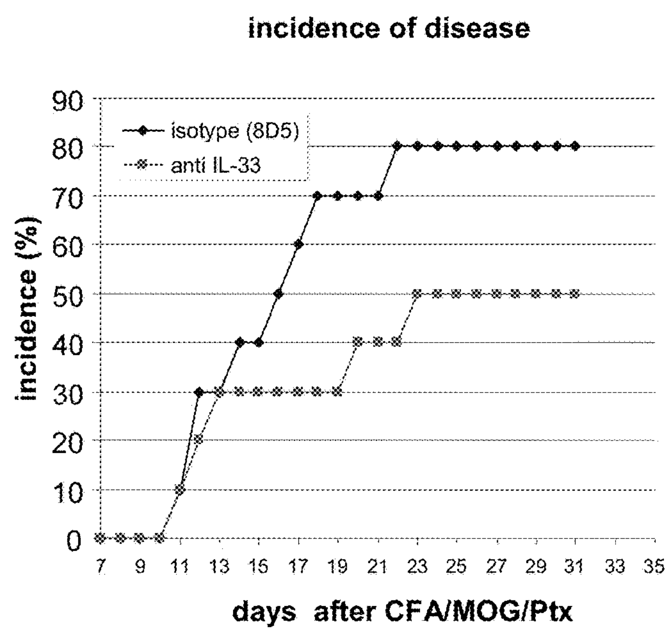
FIG. 6 shows the incidence of EAE in anti-IL-33 and isotype control treated mice.

C57BL/6 mice were immunized with 50 ug of myelin oligodendrocyte glycoprotein (MOG) peptide to induce EAE. The clinical assessment of the disease is scored as follows: 1=limp tail; 2=hind limb weakness; 3=inability to right+single hind limb weakness; 4=inability to right+single hind limb paralysis; 5=bilateral hind limb paralysis; 6=bilateral hind limb paralysis+abdomen collapse; and 7=6+moribund. EAE mice were treated subcutaneously with either 100 mg of anti-IL-33 antibody or isotype control antibody. Anti-IL-33 treated mice showed lower disease scores and lower disease incidence than the control group (see FIGS. 5 and 6).

VI. Pull-Down Assay to Identify IL-33R Complex

IL-33 was biotinylated with EX-LINK Supho-NHS-Biotin (Pierce). Pull-down of 2 μg biotinylated IL-33 was performed in 500 μl RIPA-Lysis buffer (upstate cell singaling solution) with 50 μl of a 50% Slurry of Agarose bound Avidin D (Vector Laborities). 5 μg of either recombinant extra-cellular ST2-Fc (R&D Systems) or SIGIRR-Fc (R&D Systems) was used. After incubation overnight at 4° C. precipitates were washed 3× with 500 μl RIPA-Lysis buffer. The precipitated proteins were separated by SDS-Page, electroblotted, and visualized by Western blot/ECL reaction with antibodies specific against ST2 (R&D Systems) or SIGIRR (R&D Systems). Pull-down of biotinylated IL-33 with ST2-Fc or SIGIRR-Fc was performed in the same manner as above only Protein G-Sepharose (Amersham Bioscience) was used instead of Agarose bound Avidin D. IL-33 presents was visualized via a Streptavidin-HRP conjugate (Pierce) and ECL reaction.

VII. Phosphorylation of NF-κB and MAP Kinases

The mastcell line WTMC was described previously (see, e.g., Wright, et al. (2003). *J. Immunol.* 171:3034-3046.). Cells were lysed in RIPA lysis Buffer (Upstate) containing Complete Mini protease inhibitor cocktail (Roche) and 10 mM $Na_3VO_4$. Proteins were separated by SDS-Page, transferred to Immobilon-P membranes (Millipore) and immunoblotted using antibodies to phosphorylated p65 NF-κB, p65 NF-κB, phosphorylated p44/42 MAP kinases, p44/42 MAP kinases, phosphorylated p38 MAP kinase and p38 MAP kinase (all Antibodies form Cell Signaling Technology).

VIII. Transient Transfection and Reporter Gene Assays

HEK293FT cells were seeded before transfection with an NF-κB-driven GFP reporter gene construct (pNF-κB-hrGFP; Stratagene) and with a combination of plasmids encoding for ST2, or SIGIRR or both, as indicated with Fugene-6 (Roche) according to manufacturer's recommendations. Cells were split 24 hours after transfection. After 24 hours cells were either left untreated or stimulated with mouse IL-33 at the concentration of 50 ng/ml. Sixteen hours after stimulation, cells were analyzed for GFP-expression by FACS.

TABLE 9

| Sequence Identifiers | |
|---|---|
| SEQ ID NO: 1 | Human IL-33 nucleic acid sequence |
| SEQ ID NO: 2 | Human IL-33 polypeptide sequence |
| SEQ ID NO: 3 | Mouse IL-33 nucleic acid sequence |
| SEQ ID NO: 4 | Mouse IL-33 nucleic acid sequence |
| SEQ ID NO: 5 | Human T1/ST2 nucleic acid sequence |
| SEQ ID NO: 6 | Human T1/ST2 polypeptide sequence |
| SEQ ID NO: 7 | Mouse T1/ST2 nucleic acid sequence |
| SEQ ID NO: 8 | Mouse T1/ST2 polypeptide sequence |
| SEQ ID NO: 9 | Human SIGIRR nucleic acid sequence |
| SEQ ID NO: 10 | Human SIGIRR polypeptide sequence |
| SEQ ID NO: 11 | Mouse SIGIRR nucleic acid sequence |
| SEQ ID NO: 12 | Mouse SIGIRR polypeptide sequence |

All citations herein are incorporated herein by reference to the same extent as if each individual publication, patent application, or patent was specifically and individually indicated to be incorporated by reference including all figures and drawings.

Many modifications and variations of this invention, as will be apparent to one of ordinary skill in the art can be made to adapt to a particular situation, material, composition of matter, process, process step or steps, to preserve the objective, spirit and scope of the invention. All such modifications are intended to be within the scope of the claims appended hereto without departing from the spirit and scope of the invention. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method of treating an immune disorder of asthma or allergy in a subject, comprising administering a therapeutically effective amount of an antibody or antigen binding fragment that specifically binds to IL-33 to the subject in need thereof.

2. The method of claim 1, wherein the immune disorder comprises a TH2-type response.

3. The method of claim 2, wherein the TH2-type response comprises an early event in a TH2-type response.

4. The method of claim 1, wherein the antibody or antigen binding fragment is:

a) a polyclonal antibody;

b) a monoclonal antibody;

c) a humanized antibody, or a fragment thereof; or d) a Fab, Fv, or $F(ab')_2$ fragment.

5. The method of claim 1, wherein the immune disorder is asthma.

6. The method of claim 1, wherein the immune disorder is allergy.

7. The method of claim 5, wherein the asthma comprises a TH2-type response.

8. The method of claim 6, wherein the allergy comprises a TH2-type response.

* * * * *